United States Patent
Baxter et al.

(10) Patent No.: US 9,962,321 B2
(45) Date of Patent: *May 8, 2018

(54) COMPOSITIONS PROVIDING DELAYED RELEASE OF ACTIVES

(71) Applicant: Noxell Corporation, Hunt Valley, MD (US)

(72) Inventors: Elaine Alice Marie Baxter, Twickenham (GB); Simon Richard Biggs, Chelmer (AU); Olivier Jean Cayre, Thurlstone (GB); Zoë Dyter, Newcastle Upon Tyne (GB); James Paul Hitchcock, Leeds (GB); Lynette Anne Makins Holland, Abbots Langley (GB); Madhuri Jayant Khanolkar, Singapore (SG); Raul Rodrigo Gomez, Brussels (BE); Alison Louise Tasker, Toowong (AU); David William York, Newcastle Upon Tyne (GB)

(73) Assignee: Noxell Corporation, Hunt Valley, MD (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/971,608

(22) Filed: Dec. 16, 2015

(65) Prior Publication Data

US 2016/0184196 A1 Jun. 30, 2016

Related U.S. Application Data

(60) Provisional application No. 62/092,577, filed on Dec. 16, 2014.

(51) Int. Cl.
*C11B 9/00* (2006.01)
*A61K 8/11* (2006.01)
(Continued)

(52) U.S. Cl.
CPC ............... *A61K 8/11* (2013.01); *A01N 25/28* (2013.01); *A61K 8/19* (2013.01); *A61K 9/501* (2013.01);
(Continued)

(58) Field of Classification Search
CPC ....................................................... C11B 9/00
See application file for complete search history.

(56) References Cited

U.S. PATENT DOCUMENTS 3,503,783 A * 3/1970 Evans ...................... B01J 13/22
264/4.3
4,696,863 A 9/1987 Matsushita et al.
(Continued)

FOREIGN PATENT DOCUMENTS

EP 1780731 A1 5/2007
GB 1359492 7/1974
(Continued)

OTHER PUBLICATIONS

English Machine Translation of WO2010003762 A1 Obtained Oct. 18, 2016 at: https://worldwide.espacenet.com/publicationDetails/biblio?CC=WO&NR=2010003762A1&KC=A1&FT=D&ND=3&date=20100114&DB=EPODOC&locale=en_EP#.*
(Continued)

*Primary Examiner* — Arrie L Reuther
(74) *Attorney, Agent, or Firm* — Schwegman Lundberg & Woessner, P.A.

(57) ABSTRACT

Consumer products including compositions that include coated microcapsules, said coated microcapsules including a polymeric shell and a liquid core material encapsulated therein; and a metallic coating surrounding said microcapsules and methods related thereto.

16 Claims, 9 Drawing Sheets

(51) Int. Cl.
| | |
|---|---|
| *A61Q 5/08* | (2006.01) |
| *A61Q 13/00* | (2006.01) |
| *A61K 8/19* | (2006.01) |
| *B01J 13/22* | (2006.01) |
| *A61Q 5/10* | (2006.01) |
| *A01N 25/28* | (2006.01) |
| *B01J 13/06* | (2006.01) |
| *B01J 13/14* | (2006.01) |
| *C09B 67/02* | (2006.01) |
| *C11D 3/50* | (2006.01) |
| *A61K 9/50* | (2006.01) |
| *C11D 17/00* | (2006.01) |

(52) U.S. Cl.
CPC .......... *A61K 9/5015* (2013.01); *A61K 9/5026* (2013.01); *A61Q 5/08* (2013.01); *A61Q 5/10* (2013.01); *A61Q 13/00* (2013.01); *B01J 13/06* (2013.01); *B01J 13/14* (2013.01); *B01J 13/22* (2013.01); *C09B 67/0097* (2013.01); *C11B 9/00* (2013.01); *C11B 9/0007* (2013.01); *C11B 9/0019* (2013.01); *C11D 3/505* (2013.01); *C11D 17/0039* (2013.01); *A61K 2800/412* (2013.01); *A61K 2800/56* (2013.01); *A61K 2800/61* (2013.01); *A61K 2800/621* (2013.01)

(56) References Cited

U.S. PATENT DOCUMENTS

| | | | |
|---|---|---|---|
| 4,756,906 | A | 7/1988 | Sweeny |
| 4,795,260 | A | 1/1989 | Schuur et al. |
| 4,818,522 | A | 4/1989 | Ferentchak et al. |
| 8,679,629 | B2 | 3/2014 | Zhao et al. |
| 2002/0197404 | A1 | 12/2002 | Lee et al. |
| 2005/0158390 | A1 | 7/2005 | Rana et al. |
| 2007/0098976 | A1 | 5/2007 | Lee et al. |
| 2008/0081193 | A1 | 4/2008 | Ou et al. |
| 2009/0253612 | A1 | 10/2009 | Mushock et al. |
| 2010/0325812 | A1 | 12/2010 | Panandiker et al. |
| 2011/0008427 | A1* | 1/2011 | Biggs ................. A61K 8/11 424/463 |
| 2012/0237578 | A1 | 9/2012 | Lei et al. |
| 2013/0040817 | A1* | 2/2013 | Dreher ................ A01N 25/28 504/359 |
| 2013/0045877 | A1 | 2/2013 | Yap et al. |
| 2015/0258219 | A1 | 9/2015 | Kataoka et al. |
| 2016/0168509 | A1 | 6/2016 | Hitchcock et al. |
| 2016/0168510 | A1 | 6/2016 | Tasker et al. |
| 2016/0168511 | A1 | 6/2016 | Hitchcock et al. |
| 2016/0177221 | A1 | 6/2016 | Hitchcock et al. |

FOREIGN PATENT DOCUMENTS

| | | | |
|---|---|---|---|
| GB | 2473870 | | 3/2011 |
| JP | 61225115 | | 10/1986 |
| KR | 2006096526 | | 9/2006 |
| KR | 100758786 | | 9/2007 |
| KR | 20080020857 | A | 3/2008 |
| WO | WO-2005/057163 | A2 | 6/2005 |
| WO | WO-2009/037482 | A2 | 3/2009 |
| WO | WO 2010/003762 | A1 | 1/2010 |
| WO | WO 2010003762 | A1 * | 1/2010 .............. B01J 13/22 |
| WO | WO-2014/058079 | A1 | 4/2014 |
| WO | WO-2016/100477 | A1 | 6/2016 |
| WO | WO-2016/100479 | A1 | 6/2016 |
| WO | WO-2016/100482 | A1 | 6/2016 |
| WO | WO-2016/100492 | A1 | 6/2016 |
| WO | WO-2016/100499 | A1 | 6/2016 |

OTHER PUBLICATIONS

PCT International Search Report dated Feb. 26, 2016—5 pages.
PCT International Search Report dated Apr. 25, 2016—4 pages.
PCT International Search Report dated Apr. 5, 2016—5 pages.
All Office Actions U.S. Appl. No. 14/971,645.
All Office Actions U.S. Appl. No. 14/971,754.
All Office Actions U.S. Appl. No. 14/971,783.
All Office Actions U.S. Appl. No. 14/971,805.
Olivier J. Cayre, Polymer Based Functional Particulates: Design, Synthesis and Applications, University of Loughborough, pp. 1-44, Nov. 2014.
Andrew Loxley, et al., "Preparation of Poly(methylmethacrylate) Microcapsules with Liquid Cores", Journal of Colloid and Interface Science, vol. 208, No. 1, pp. 49-62, Dec. 1, 1998.
Horiuchi, et al., "Platinum Colloid Catalyzed Etchingless Gold Electroless Plating with Strong Adhesion to Polymers", Surface and Coating Technology, vol. 204, pp. 3811-3817, 2010.
Tatsuo, et al., "Preparation of Polymer Core-Shell Particles Supporting Gold Nanoparticles", Colloids and Surfaces A: Physiocochemical and Engineering Aspects, vol. 377, pp. 63-69, 2011.
Conghui, et al., "Platinum-Nanoparticle Supported Core-Shell Polymer Nanospheres with Unexpected Water Stability and Facile Further Modification", Nanotechnology, vol. 23, 9 pages, Apr. 5, 2012.
Song, et al. "Thermal Stability of Composite Phase Change Material Microcapsules Incorporated with Silver Nano-Particles", Polymer, vol. 48, pp. 3317-3323, 2007.
Lin, et al., "Preparation of PMMA-Ni Core-Shell Composite Particles by Electroless Plating on Polyelectrolyte-Modified PMMA Beads", Applied Surface Science, vol. 282, pp. 741-745, 2013.
Kim, et al., "Synthesis and Electrical Resistivity of the Monodisperse PMMA/Ag Hybrid Particles", Materials Chemistry and Physics, vol. 134, pp. 814-820, 2012, Inha University, Republic of Korea.
Patchan, et al., "Liquid Filled Metal Microcapsules", ACS Appl. Mater. Interfaces, vol. 4, pp. 2406-2412, 2012, The John Hopkins University, USA.
"U.S. Appl. No. 14/971,645, Final Office Action dated May 10, 2017", 13 pgs.
"U.S. Appl. No. 14/971,645, Preliminary Amendment dated Mar. 8, 2016", 8 pgs.
"U.S. Appl. No. 14/971,645, Response dated Mar. 23, 2017 to Non Final Office Action dated Oct. 26, 2016", 10 pgs.
"U.S. Appl. No. 14/971,645, Response dated Aug. 23, 2016 to Restriction Requirement dated Jun. 28, 2016", 1 pg.
"U.S. Appl. No. 14/971,754, Non Final Office Action dated Jan. 26, 2017", 22 pgs.
"U.S. Appl. No. 14/971,754, Preliminary Amendment dated Feb. 26, 2016", 7 pgs.
"U.S. Appl. No. 14/971,754, Response dated Jul. 26, 2017 to Non Final Office Action dated Jan. 26, 2017", 9 pgs.
"U.S. Appl. No. 14/971,783, Non Final Office Action dated Feb. 1, 2017", 23 pgs.
"U.S. Appl. No. 14/971,783, Preliminary Amendment dated Feb. 26, 2016", 6 pgs.
"U.S. Appl. No. 14/971,805, Final Office Action dated May 10, 2017", 12 pgs.
"U.S. Appl. No. 14/971,805, Non Final Office Action dated Oct. 27, 2016", 23 pgs.
"U.S. Appl. No. 14/971,805, Preliminary Amendment dated Jan. 26, 2016", 7 pgs.
"U.S. Appl. No. 14/971,805, Preliminary Amendment dated Feb. 26, 2016", 5 pgs.
"U.S. Appl. No. 14/971,805, Respnose dated Mar. 23, 2017 to Non Final Office Action dated Oct. 27, 2016", 10 pgs.
"U.S. Appl. No. 14/971,805, Response dated Aug. 23, 2016 to Restriction Requirement dated Jun. 28, 2016", 1 pgs.
"U.S. Appl. No. 14/971,805, Restriction Requirement dated Jun. 28, 2016", 6 pgs.
"English Translation of WO 2010003762A1, published Jan. 14, 2010", [Online]. Retrieved from the Internet: <URL: https://worldwide.espacenet.com/publicationDetails/biblio?CC=WO&NR=2010003762A1&KC=A1&FT=D&ND=3&date=20100114&DB=EPODOC&locale=en_EP#>, (2016), 21 pgs.

(56) References Cited

OTHER PUBLICATIONS

"International Application Serial No. PCT/US2015/066041, Written Opinion dated Feb. 26, 2016", 6 pgs.
"International Application Serial No. PCT/US2015/066043, Written Opinion dated Apr. 25, 2016", 5 pgs.
"International Application Serial No. PCT/US2015/066048, Written Opinion dated Apr. 5, 2016", 5 pgs.
"International Application Serial No. PCT/US2015/066059, Written Opinion dated Apr. 5, 2016", 4 pgs.
"International Application Serial No. PCT/US2015/066067, International Search Report dated Apr. 25, 2016", 3 pgs.
Qingwen, Song, et al., "Thermal stability of composite phase change material microcapsules incorporated with silver", *Polymer*, 48(11), (May 11, 2007), 3317-3323.
Tatsuo, Taniguchi, et al., "Preparation of polymer coreshell particles supporting gold nanoparticles", *Colloids and Surfaces A; Physicochemical and Engineering Aspects*, 377(1), (Dec. 10, 2010), 63-69.
Yuan, Conghui, et al., "Platinum-nanoparticle-supported core shell polymer nanospheres with unexpected water stability and facile further modification", *Nanotechnology*, 23(17), 175301, (2012), 9 pgs.

\* cited by examiner

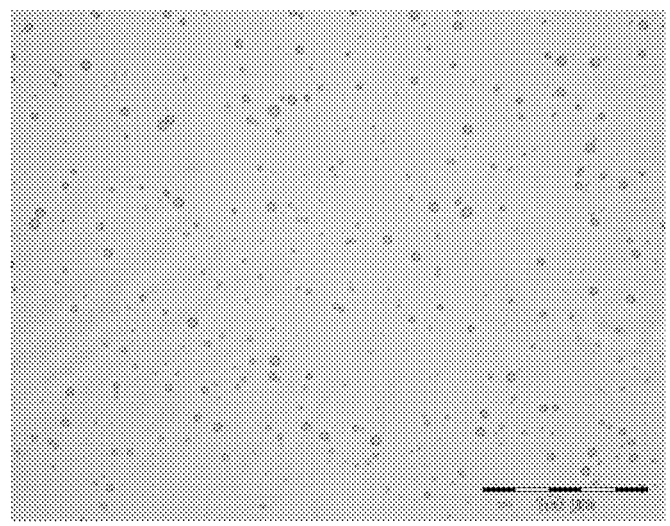
Fig. 3A
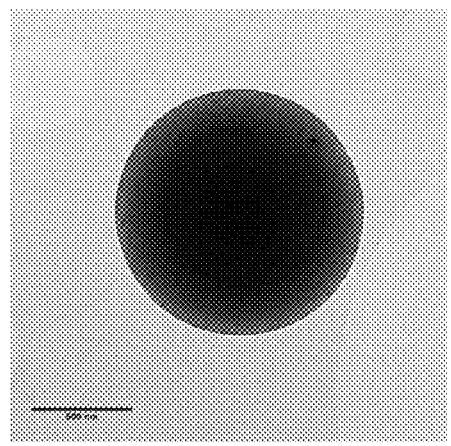 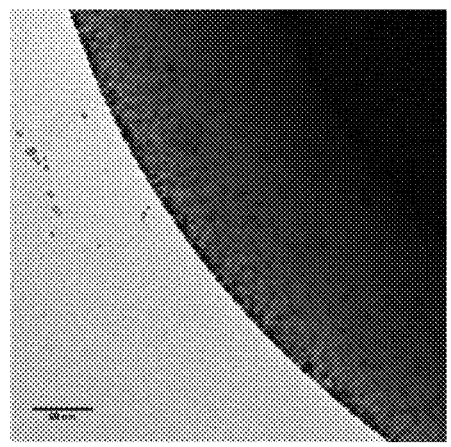
Fig. 3B                Fig. 3C

US 9,962,321 B2

COMPOSITIONS PROVIDING DELAYED RELEASE OF ACTIVES

TECHNICAL FIELD

The present disclosure generally relates to consumer products and methods of making a consumer product including microcapsules that contain a liquid core material.

BACKGROUND

Various processes for microencapsulation are known. Unfortunately, many microcapsules manufactured have drawbacks that include, but are not limited to: (1) they cannot be formulated in certain classes of products due to strict formulation limits, (2) they are highly permeable when incorporated into certain products such as those that contain high levels of surfactant, solvents, and/or water, resulting in the premature release of the active, (3) they can only effectively encapsulate a limited breadth of actives, and (4) they either are so stable that they do not release the active in use or have insufficient mechanical stability to withstand the processes required to incorporate them in and/or make a consumer product and (5) they do not adequately deposit on the situs that is being treated with consumer product that contains the microcapsules. Thus, there exists a need for microcapsules that can improve on some of these known drawbacks.

SUMMARY

A consumer product comprising a composition, said composition comprising: an adjunct material; and a plurality of coated microcapsules, said coated microcapsule comprising i) a microcapsule comprising a polymeric shell and a liquid core material encapsulated therein; and ii) a metallic coating surrounding said microcapsule; wherein the metallic coating comprises particles of a first metal adsorbed on said polymeric shell and a film of a second metal formed thereon; and wherein the metallic coating has a maximum thickness of 1000 nm.

A consumer product comprising a composition, said composition comprising: from 50% to 99.9%, by weight of the composition of ethanol; and a plurality of coated microcapsules, said coated microcapsule comprising i) a microcapsule comprising a polymeric shell and a liquid core material encapsulated therein; and ii) a metallic coating surrounding said microcapsule; wherein the metallic coating comprises particles of a first metal adsorbed on said polymeric shell and a film of a second metal formed thereon; and wherein the metallic coating has a maximum thickness of 1000 nm; optionally, wherein the coated microcapsules retain more than 50% by weight of the liquid core material when tested under the Ethanol Stability Test described herein.

A method of making a composition, said method comprising: combining an adjunct material with a plurality of coated microcapsules to form a composition; wherein said coated microcapsules comprise i) a microcapsule comprising a polymeric shell and a liquid core material encapsulated therein; and ii) a metallic coating surrounding said microcapsule; wherein the metallic coating comprises particles of a first metal adsorbed on said polymeric shell and a film of a second metal formed thereon; and wherein the metallic coating has a maximum thickness of 1000 nm; wherein said composition is a component of a consumer product.

BRIEF DESCRIPTION OF THE DRAWINGS

While the specification concludes with claims, it is believed that the same will be better understood from the following description taken in conjunction with the accompanying drawings in which:

FIG. 1A is converted to an uncoated microcapsule FIG. 1B comprising a polymeric shell and a liquid core material. Particles of a first metal are adsorbed onto the microcapsule surface FIG. 1C and a continuous film of a second metal is then applied, yielding a coated microcapsule FIG. 1D. Shown beneath the schematic diagram are corresponding optical microscopy FIG. 1A, transmission electron microscopy (TEM) (FIGS. 1B and 1C) and scanning electron microscopy (SEM) FIG. 1D images of a microcapsule formed by such a process.

FIG. 2A an SEM image of the uncoated microcapsules; FIG. 2B a TEM image showing the platinum nanoparticles adsorbed on the outer surface of the microcapsules; and FIG. 2C an SEM image showing the continuous gold film.

FIGS. 3A, 3B, 3C, 3D and 3E provide optical, SEM and TEM images obtained at various stages of preparation of a coated microcapsule, the microcapsule comprising a PEMA shell, a toluene core and a metallic coating comprising a continuous silver film formed on a layer of borohydride-stabilised gold nanoparticles. Shown are: FIG. 3A an optical image showing the uncoated microcapsules; FIG. 3B and FIG. 3C, TEM images showing the borohydride-stabilised gold nanoparticles adsorbed on the surface of the microcapsules; and FIG. 3D an SEM image showing the continuous silver film. Also shown is: FIG. 3E an EDX graph indicating the silver content of the metallic film.

FIG. 6A an optical micrograph showing the uncoated microcapsules; FIG. 6B a TEM image showing the PVP-stabilised platinum nanoparticles adsorbed on the surface of the microcapsules; and FIG. 6C an SEM image showing the gold film on the microcapsules.

DETAILED DESCRIPTION

Figures 1A, 1B, 1C, 1D:
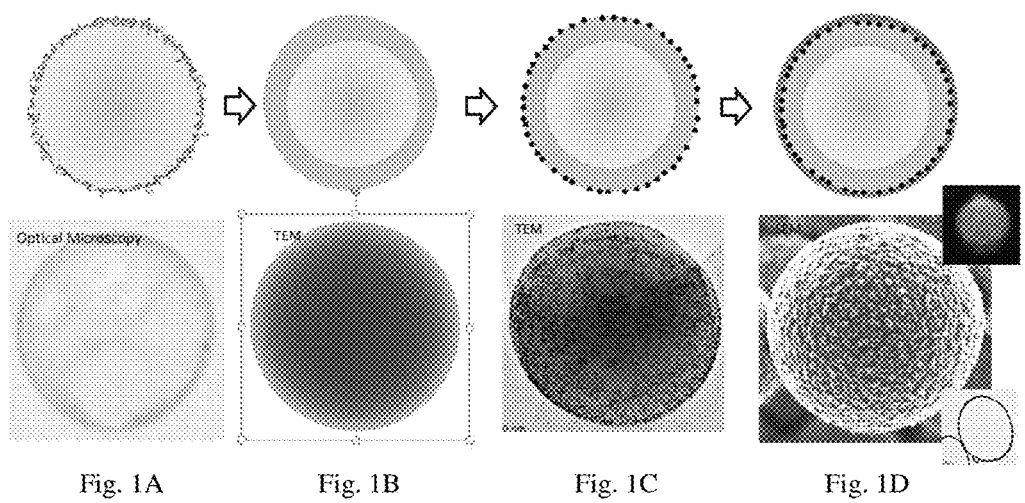
FIGS. 1A, 1B, 1C and 1D depict a schematic diagram illustrating a process for preparing an exemplary coated microcapsule wherein a schematic diagram is in the upper portion and beneath the schematic diagram is the corresponding microscopy. The upper schematic diagram illustrates a process for preparing an exemplary coated microcapsule. In the depicted process, emulsion template

All percentages are weight percentages based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Adjunct material" is any material that is not a microcapsule (coated or uncoated) and that is added to the microcapsules (coated or uncoated) to form the consumer product. The adjunct material may take many forms, and it is to be appreciated that an adjunct material may be a pure substance or include more than one type of material such that the adjunct material is collection/mixture of different materials, arranged in any manner. Adjunct materials, however, are limited to those used in consumer products.

"Free of" means that the stated ingredient has not been added to the composition. However, the stated ingredient may incidentally form as a byproduct or a reaction product of the other components of the composition.

"Nonvolatile" refers to those materials that liquid or solid under ambient conditions and have a measurable vapor pressure at 25° C. These materials typically have a vapor pressure of less than about 0.0000001 mmHg, and an average boiling point typically greater than about 250° C.

"Soluble" means at least about 0.1 g of solute dissolves in 100 ml of solvent at 25° C. and 1 atm of pressure.

"Substantially free of" means an amount of a material that is less than about 1%, 0.5%, 0.25%, 0.1%, 0.05%, 0.01%, or 0.001% by weight of a composition.

"Derivatives" as used herein, include but are not limited to, amide, ether, ester, amino, carboxyl, acetyl, and/or alcohol derivatives of a given chemical.

"Skin care actives" as used herein, means substances that when applied to the skin, provide a benefit or improvement to the skin. It is to be understood that skin care actives are useful not only for application to skin, but also to hair, nails and other mammalian keratinous tissue.

"Situs" means the location where the composition is applied. Non-limiting examples of a situs include mammalian keratinous tissue and clothing.

"Volatile," as used herein, unless otherwise specified, refers to those materials that are liquid or SOLID under ambient conditions and which have a measurable vapor pressure at 25° C. These materials typically have a vapor pressure of greater than about 0.0000001 mmHg, alternatively from about 0.02 mmHg to about 20 mmHg, and an average boiling point typically less than about 250° C., alternatively less than about 235° C.

When the stability of microcapsule is compromised by inclusion in a composition, a potential solution is to separate the microcapsule from the composition by using a container with separate reservoirs for storing the incompatible ingredients. However, separating the microcapsules from the composition is not always a viable option. Accordingly, the coated microcapsules disclosed can be made to better control permeability characteristics of actives. In this regard, the coated microcapsules disclosed herein are surprisingly better able to contain liquid contents without leakage over time.

Liquid Core Material

The coated microcapsules may comprise a liquid core material encapsulated by a polymeric shell. The term "liquid core material" as used herein refers to a core material formed of one or more components, at least 90% by weight of which are liquid at standard ambient temperature and pressure. The term "standard ambient temperature and pressure" (or "STP") refers to a temperature of 25° C. and an absolute pressure of 100 kPa. Preferably, the liquid core material comprises at least 95% by weight, e.g. at least 98% by weight, of one or more components which are liquid at standard ambient temperature and pressure. In some examples, the liquid core material consists of one or more components which are liquid at standard ambient temperature and pressure. In some examples, the liquid core material includes a mixture of liquids and a solid, non-limiting examples of which include a mixture of vanillin and perfume oils.

The liquid core material may be present in the coated microcapsule in an amount of at least 1% by weight of the microcapsule, preferably in an amount of at least 30% by weight, and more preferably in an amount of at least 60% by weight. In some examples, the liquid core material is present in the coated microcapsule in an amount of from 10 to 99.9% by weight of the coated microcapsule, alternatively from 40 to 90% by weight of the coated microcapsule, alternatively from 50 to 90% by weight, alternatively from 60 to 80% by weight.

In some examples, the liquid core material comprises one or more components which are volatile. Unless otherwise specified, the term "volatile" as used herein refers to those materials that are liquid or solid under ambient conditions and which have a measurable vapour pressure at 25° C. These materials typically have a vapour pressure of greater than about 0.0000001 mm Hg, e.g. from about 0.02 mm Hg to about 20 mm Hg, and an average boiling point typically less than about 250° C., e.g. less than about 235° C.

The liquid core material may consist of a single material or it may be formed of a mixture of different materials. In some examples, the liquid core material comprises one or more active ingredients. The coated microcapsules described herein are useful with a wide variety of active ingredients (i.e. "core materials") including, by way of illustration and without limitation, perfumes; brighteners; insect repellants; silicones; waxes; flavors; vitamins; fabric softening agents; depilatories; skin care agents; enzymes; probiotics; dye polymer conjugate; dye clay conjugate; perfume delivery system; sensates in one aspect a cooling agent; attractants, in one aspect a pheromone; anti-bacterial agents; dyes; pigments; bleaches; flavorants; sweeteners; waxes; pharmaceuticals; fertilizers; herbicides and mixtures thereof. The microcapsule core materials can include materials which alter rheology or flow characteristics, or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. Particularly useful encapsulated materials are volatile fragrances.

The liquid core material preferably comprises one or more components which are oil-soluble. The use of a liquid core material which is oil-soluble will be preferable having regard to, inter alia, the production of the microcapsules, which will typically be prepared by a process which involves the use of an oil-in-water emulsion in which the liquid core material is present in the non-aqueous (oil) phase. In some examples, the liquid core material is substantially free of water. In particular, the amount of water present in the liquid core material may be less than 5% by weight, e.g. less than 1% by weight, of the liquid core material. More preferably, the liquid core material consists of one or more oil-soluble components.

The liquid core material is preferably free of compounds which are capable of reacting with any of the compounds that are used to form the polymeric shell of the microcapsules. In particular, the liquid core material is preferably free of any polymerisable compounds.

In some examples, the liquid core material comprises a perfume oil formed of one or more perfume raw materials. The term "perfume oil" as used herein refers to the perfume raw material, or mixture of perfume raw materials, that is used to impart an overall pleasant odour profile to the liquid core material. Thus, where different perfume raw materials are present in the liquid core material, this term refers to the overall mixture of perfume raw materials in the liquid core material. The choice of the perfume raw materials defines both the odour intensity and character of the liquid core material. The perfume oils utilised in the coated microcapsules may be relatively simple in their chemical make-up, for example consisting of only a single perfume raw material, or they may comprise complex mixtures of perfume raw materials, all chosen to provide a desired odour.

The perfume oil may comprise one or more perfume raw materials having a boiling point of less than 500° C., e.g. less than 400° C., e.g. less than 350° C. The boiling points of many perfume raw materials are given in, e.g., "Perfume and Flavor Chemicals (Aroma Chemicals)" by Steffen Arctander (1969) and other textbooks known in the art.

The one or more perfume raw materials will typically be hydrophobic. The hydrophobicity of a given compound may be defined in terms of its partition coefficient. The term "partition coefficient" as used herein refers to the ratio between the equilibrium concentration of that substance in n-octanol and in water, and is a measure of the differential solubility of said substance between these two solvents. Partition coefficients are described in more detail in U.S. Pat. No. 5,578,563.

The term "log P" refers to the logarithm to the base 10 of the partition coefficient. Values of log P values can be readily calculated using a program called "CLOGP" which is available from Daylight Chemical Information Systems Inc., 30 Irvine Calif., U.S.A. or using Advanced Chemistry Development (ACD/Labs) Software 13375P 9 V11.02 (© 1994-2014 ACD/Labs).

In some examples, the perfume oil comprises one or more perfume raw materials having a calculated log P (C log P) value of about −0.5 or greater, e.g. greater than 0.1, e.g. greater than 0.5, e.g. greater than 1.0. In some examples, the perfume oil consists of one or more perfume raw materials having a C log P value of greater than 0.1, e.g. greater than 0.5, e.g. greater than 1.0.

In some examples, the perfume oil comprises one or more perfume raw materials selected from aldehydes, esters, alcohols, ketones, ethers, alkenes, nitriles, Schiff bases, and mixtures thereof.

Examples of aldehyde perfume raw materials include, without limitation, alpha-amylcinnamaldehyde, anisic aldehyde, decyl aldehyde, lauric aldehyde, methyl n-nonyl acetaldehyde, methyl octyl acetaldehyde, nonylaldehyde, benzenecarboxaldehyde, neral, geranial, 1,1-diethoxy-3,7-dimethylocta-2,6-diene, 4-isopropylbenzaldehyde, 2,4-dimethyl-3-cyclohexene-1-carboxaldehyde, alpha-methyl-p-isopropyldihydrocinnamaldehyde, 3-(3-isopropylphenyl) butanal, alpha-hexylcinnamaldehyde, 7-hydroxy-3,7-dimethyloctan-1-al, 2,4-dimethyl-3-cyclohexene-1-carboxaldehyde, octyl aldehyde, phenylacetaldehyde, 2,4-dimethyl-3-cyclohexene-1-carboxaldehyde, hexanal, 3,7-dimethyloctanal, 6,6-dimethylbicyclo[3.1.1]hept-2-ene-2-butanal, nonanal, octanal, 2-nonenal undecenal, 2-methyl-4-(2,6,6-trimethyl-1-cyclohexenyl-1)-2-butenal, 2,6-dimethyloctanal, 3-(p-isopropylphenyl)propionaldehyde, 3-phenyl-4-pentenal citronellal, o/p-ethyl-alpha, alpha, 9-decenal, dimethyldihydrocinnamaldehyde, p-isobutyl-alphamethylydrocinnamaldehyde, cis-4-decen-1-al, 2,5-dimethyl-2-ethenyl-4-hexenal, trans-2-methyl-2-butenal, 3-methylnonanal, alpha-sinensal, 3-phenylbutanal, 2,2-dimethyl-3-phenylpropionaldehyde, m-tertbutyl-alpha-methyl-dihydrocinnamic aldehyde, geranyl oxyacetaldehyde, trans-4-decen-1-al, methoxycitronellal, and mixtures thereof.

Examples of ester perfume raw materials include, without limitation, allyl cyclohexane-propionate, allyl heptanoate, allyl amyl glycolate, allyl caproate, amyl acetate (n-pentyl acetate), amyl propionate, benzyl acetate, benzyl propionate, benzyl salicylate, cis-3-hexenylacetate, citronellyl acetate, citronellyl propionate, cyclohexyl salicylate, dihydro isojasmonate, dimethyl benzyl carbinyl acetate, ethyl acetate, ethyl acetoacetate, ethyl butyrate, ethyl-2-methyl butryrate, ethyl-2-methyl pentanoate, fenchyl acetate (1,3,3-trimethyl-2-norbornanyl acetate), tricyclodecenyl acetate, tricyclodecenyl propionate, geranyl acetate, cis-3-hexenyl isobutyrate, hexyl acetate, cis-3-hexenyl salicylate, n-hexyl salicylate, isobornyl acetate, linalyl acetate, p-t-butyl cyclohexyl acetate, (−)-L-menthyl acetate, o-t-butylcyclohexyl acetate, methyl benzoate, methyl dihydro isojasmonate, alpha-methylbenzyl acetate, methyl salicylate, 2-phenylethyl acetate, prenyl acetate, cedryl acetate, cyclabute, phenethyl phenylacetate, terpinyl formate, citronellyl anthranilate, ethyl tricyclo[5.2.1.0-2,6]decane-2-carboxylate, n-hexyl ethyl acetoacetate, 2-tertbutyl-4-methyl cyclohexyl acetate, formic acid, 3,5,5-trimethylhexyl ester, phenethyl crotonate, cyclogeranyl acetate, geranyl crotonate, ethyl geranate, geranyl isobutyrate, 3,7-dimethyl-ethyl 2-nonynoate-2,6-octadienoic acid methyl ester, citronellyl valerate, 2-hexenyl-cyclopentanone, cyclohexyl anthranilate, L-citronellyl tiglate, butyl tiglate, pentyl tiglate, geranyl caprylate, 9-decenyl acetate, 2-isopropyl-5-methylhexyl-1 butyrate, n-pentyl benzoate, 2-methylbutyl benzoate (and mixtures thereof with pentyl benzoate), dimethyl benzyl carbinyl propionate, dimethyl benzyl carbinyl acetate, trans-2-hexenyl salicylate, dimethyl benzyl carbinyl isobutyrate, 3,7-dimethyloctyl formate, rhodinyl formate, rhodinyl isovalerate, rhodinyl acetate, rhodinyl butyrate, rhodinyl propionate, cyclohexylethyl acetate, neryl butyrate, tetrahydrogeranyl butyrate, myrcenyl acetate, 2,5-dimethyl-2-ethenylhex-4-enoic acid, methyl ester, 2,4-dimethylcyclohexane-1-methyl acetate, ocimenyl acetate, linalyl isobutyrate, 6-methyl-5-heptenyl-1 acetate, 4-methyl-2-pentyl acetate, n-pentyl 2-methylbutyrate, propyl acetate, isopropenyl acetate, isopropyl acetate, 1-methylcyclohex-3-ene-carboxylic acid, methyl ester, propyl tiglate, propyl/isobutyl cyclopent-3-enyl-1-acetate (alphavinyl), butyl 2-furoate, ethyl 2-pentenoate, (E)-methyl 3-pentenoate, 3-methoxy-3-methylbutyl acetate, n-pentyl crotonate, n-pentyl isobutyrate, propyl formate, furfuryl butyrate, methyl angelate, methyl pivalate, prenyl caproate, furfuryl propionate, diethyl malate, isopropyl 2-methylbutyrate, dimethyl malonate, bornyl formate, styralyl acetate, 1-(2-furyl)-1-propanone, 1-citronellyl acetate, 3,7-dimethyl-1,6-nonadien-3-yl acetate, neryl crotonate, dihydromyrcenyl acetate, tetrahydromyrcenyl acetate, lavandulyl acetate, 4-cyclooctenyl isobutyrate, cyclopentyl isobutyrate, 3-methyl-3-butenyl acetate, allyl acetate, geranyl formate, cis-3-hexenyl caproate, and mixtures thereof.

Examples of alcohol perfume raw materials include, without limitation, benzyl alcohol, beta-gamma-hexenol (2-hexen-1-ol), cedrol, citronellol, cinnamic alcohol, p-cresol, cumic alcohol, dihydromyrcenol, 3,7-dimethyl-1-octanol, dimethyl benzyl carbinol, eucalyptol, eugenol, fenchyl alcohol, geraniol, hydratopic alcohol, isononyl alcohol (3,5,5-trimethyl-1-hexanol), linalool, methyl chavicol (estragole), methyl eugenol (eugenyl methyl ether), nerol, 2-octanol, patchouli alcohol, phenyl hexanol (3-methyl-5-phenyl-1-pentanol), phenethyl alcohol, alpha-terpineol, tetrahydrolinalool, tetrahydromyrcenol, 4-methyl-3-decen-5-ol, 1-3,7-dimethyloctane-1-ol, 2-(furfuryl-2)-heptanol, 6,8-dimethyl-2-nonanol, ethyl norbornyl cyclohexanol, beta-methyl cyclohexane ethanol, 3,7-dimethyl-(2),6-octen (adien)-1-ol, trans-2-undecen-1-ol, 2-ethyl-2-prenyl-3-hexenol, isobutyl benzyl carbinol, dimethyl benzyl carbinol, ocimenol, 3,7-dimethyl-1,6-nonadien-3-ol (cis & trans), tetrahydromyrcenol, alpha-terpineol, 9-decenol-1, 2-(2-hexenyl)-cyclopentanol, 2,6-dimethyl-2-heptanol, 3-methyl-1-octen-3-ol, 2,6-dimethyl-5-hepten-2-ol, 3,7,9-trimethyl-1,6-decadien-3-ol, 3,7-dimethyl-6-nonen-1-ol, 3,7-dimethyl-1-octyn-3-ol, 2,6-dimethyl-1,5,7-octatrienol-3, dihydromyrcenol, 2,6,-trimethyl-5,9-undecadienol, 2,5-dimethyl-2-propylhex-4-enol-1, (Z)-3-hexenol, o,m,p-methylphenylethanol, 2-methyl-5-phenyl-1-pentanol, 3-methylphenethyl alcohol, para-methyl dimethyl benzyl carbinol, methyl benzyl carbinol, p-methylphenylethanol, 3,7-dimethyl-2-octen-1-ol, 2-methyl-6-methylene-7-octen-4-ol, and mixtures thereof.

Examples of ketone perfume raw materials include, without limitation, oxacycloheptadec-10-en-2-one, benzylacetone, benzophenone, L-carvone, cis-jasmone, 4-(2,6,6-trimethyl-3-cyclohexen-1-yl)-but-3-en-4-one, ethyl amyl ketone, alpha-ionone, ionone beta, ethanone, octahydro-2,3,8, 8-tetramethyl-2-acetonaphthalene, alpha-irone, 1-(5,5-dimethyl-1-cyclo-hexen-1-yl)-4-penten-1-one, 3-nonanone, ethyl hexyl ketone, menthone, 4-methyl-acetophenone, gamma-methyl ionone, methyl pentyl ketone, methyl heptenone (6-methyl-5-hepten-2-one), methyl heptyl ketone, methyl hexyl ketone, delta muscenone, 2-octanone, 2-pentyl-3-methyl-2-cyclopenten-1-one, 2-heptylcyclopentanone, alpha-methylionone, 3-methyl-2-(trans-2-pentenyl)-cyclopentenone, octenyl cyclopentanone, n-amylcyclopentenone, 6-hydroxy-3,7-dimethyloctanoic acid lactone, 2-hydroxy-2-cyclohexen-1-one, 3-methyl-4-phenyl-3-buten-2-one, 2-pentyl-2,5,5-trimethylcyclopentanone, 2-cyclopentylcyclopentanol-1, 5-methylhexan-2-one, gamma-dodecalactone, delta-dodecalactone delta-dodecalactone, gamma-nonalactone, delta-nonalactone, gamma-octalactone, delta-undecalactone, gamma-undecalactone, and mixtures thereof.

Examples of ether perfume raw materials include, without limitation, p-cresyl methyl ether, 4,6,6,7,8,8-hexamethyl-1,3,4,6,7,8-hexahydro-cyclopenta(G)-2-benzopyran, beta-naphthyl methyl ether, methyl isobutenyl tetrahydropyran, 5-acetyl-1,1,2,3,3,6-hexamethylindan (phantolide), 7-acetyl-1,1,3,4,4,6-hexamethyltetralin (tonalid), 2-phenyl-ethyl-3-methylbut-2-enyl ether, ethyl geranyl ether, phenylethyl isopropyl ether, and mixtures thereof.

Examples of alkene perfume raw materials include, without limitation, allo-ocimene, camphene, beta-caryophyllene, cadinene, diphenylmethane, d-limonene, lymolene, beta-myrcene, para-cymene, 2-alpha-pinene, beta-pinene, alpha-terpinene, gamma-terpinene, terpineolene, 7-methyl-3-methylene-1,6-octadiene, and mixtures thereof.

Examples of nitrile perfume raw materials include, without limitation, 3,7-dimethyl-6-octenenitrile, 3,7-dimethyl-2 (3), 6-nonadienenitrile, (2E,6Z)-2,6-nonadienenitrile, n-dodecane nitrile, and mixtures thereof.

Examples of Schiff base perfume raw materials include, without limitation, citronellyl nitrile, nonanal/methyl anthranilate, N-octylidene-anthranilic acid methyl ester, hydroxycitronellal/methyl anthranilate, cyclamen aldehyde/methyl anthranilate, methoxyphenylpropanal/methyl anthranilate, ethyl p-aminobenzoate/hydroxycitronellal, citral/methyl anthranilate, 2,4-dimethylcyclohex-3-enecarbaldehyde methyl anthranilate, hydroxycitronellal-indole, and mixtures thereof.

Non-limiting examples of other the perfume raw materials useful herein include pro-fragrances such as acetal pro-fragrances, ketal pro-fragrances, ester pro-fragrances, hydrolyzable inorganic-organic pro-fragrances, and mixtures thereof. The fragrance materials may be released from the pro-fragrances in a number of ways. For example, the fragrance may be released as a result of simple hydrolysis, or by a shift in an equilibrium reaction, or by a pH-change, or by enzymatic release.

In some examples, the perfume oil comprises one or more of the perfume raw materials recited in the above lists. In some examples, the perfume oil comprises a plurality of perfume raw materials recited in the above lists.

In some examples, the liquid core material comprises one or more perfume oils of natural origin. In some examples, the liquid core material comprises one or more perfume oils selected from musk oil, civet, castoreum, ambergris, nutmeg extract, cardamon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomile oil, clove oil, sage oil, neroli oil, labdanum oil, eucalyptus oil, verbena oil, mimosa extract, narcissus extract, carrot seed extract, jasmine extract, olibanum extract, rose extract, and mixtures thereof. One or more of these perfume oils may be used with one or more of the perfume raw materials recited above.

The perfume oil may be present in the liquid core material in an amount of from 0.1 to 100% by weight of the liquid core material. In some examples, the liquid core material consists essentially, e.g. consists of, a perfume oil. In some examples, the perfume oil is present in the liquid core material in an amount of at least 10% by weight of the liquid core material, preferably at least 20% by weight, and more preferably at least 30% by weight. In some examples, the perfume oil is present in the liquid core material in an amount of from 80-100% by weight of the liquid core material, alternatively less than 80% by weight of the liquid core material, alternatively less than 70% by weight, alternatively less than 60% by weight. In some examples, the perfume oil is present in an amount of from 10 to 50% by weight of the liquid core material, more preferably from 15 to 30%. Preferred liquid core materials contain from 10 to 80% by weight of a perfume oil, preferably from 20 to 70%, more preferably from 30 to 60%.

The liquid core material may comprise one or more components in addition to the perfume oil. For example, the liquid core material may comprise one or more diluents. Examples of diluents include mono-, di- and tri-esters of $C_4$-$C_{24}$ fatty acids and glycerine, isopropyl myristate, soybean oil, hexadecanoic acid, methyl ester, isododecane, and mixtures thereof. Where present, diluents are preferably present in the liquid core material in an amount of at least 1% by weight of the liquid core material, e.g. from 10 to 60% by weight of the liquid core material.

Polymeric Shell

The liquid core material is encapsulated by a polymeric shell. The coated microcapsules may be prepared by first forming the polymeric shell around the liquid core material to as to form an uncoated microcapsule, and subsequently forming the metallic coating. The term "uncoated microcapsule" as used herein refers to the microcapsule comprising the liquid core material prior to coating with the metallic coating.

The polymeric shell may comprise one or more polymeric materials. For example, the polymeric shell may comprise one or more polymers chosen from synthetic polymers, naturally-occurring polymers, and combinations thereof. Examples of synthetic polymers include, without limitation, nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and combinations thereof. Examples of synthetic polymers include, without limitation, silk, wool, gelatin, cellulose, alginate, proteins, and combinations thereof. The polymeric shell may comprise a homopolymer or a copolymer (e.g. a block copolymer or a graft copolymer).

In some examples, the polymeric shell comprises a polyacrylate, e.g. poly(methyl methacrylate) (PMMA) or poly (ethyl methacrylate) (PEMA). The polyacrylate may be present in an amount of at least 5%, at least 10%, at least 25%, at least 30%, at least 50%, at least 70%, or at least 90% of the weight of the polymeric shell.

In some examples, the polymeric shell comprises a polyacrylate random copolymer. For example, the polyacrylate random copolymer can comprise: an amine content of from 0.2 to 2.0% by weight of the total polyacrylate mass; a carboxylic acid content of from 0.6 to 6.0% by weight of the total polyacrylate mass; and a combination of an amine content of from 0.1 to 1.0% and a carboxylic acid content of from 0.3 to 3.0% by weight of the total polyacrylate mass.

In some examples, the microcapsule shell comprises a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. In some examples, said amine is selected from the group consisting of aminoalkyl acrylates, alkyl aminoalkyl acrylates, dialkyl aminoalkyl acrylates, aminoalkyl methacrylates, alkylamino aminoalkyl methacrylates, dialkyl aminoalkyl methacrylates, tertiarybutyl aminoethyl methacrylates, diethylaminoethyl methacrylates, dimethylaminoethyl methacrylates, dipropylaminoethyl methacrylates, and mixtures thereof. In some examples, said amine is an aminoalkyl acrylate or aminoalkyl methacrylate.

In some examples, the polymeric shell comprises a reaction product of an amine with an aldehyde. For example, the polymeric shell may comprise a reaction product selected from urea cross-linked with formaldehyde or glutaraldehyde; melamine cross-linked with formaldehyde; gelatin-polyphosphate coacervates optionally cross-linked with gluteraldehyde; gelatin-gum arabic coacervates; cross-linked silicone fluids; polyamines reacted with polyisocyanates; acrylate monomers polymerized via free radical polymerization, and mixtures thereof. In some examples, the polymeric shell comprises a reaction product selected from urea-formaldehyde (i.e. the reaction product of urea cross-linked with formaldehyde) and melamine resin (i.e. melamine cross-linked with formaldehyde).

In some examples, the polymeric shell comprises gelatin, optionally in combination with one or more additional polymers. In some examples, the polymeric shell comprises gelatin and polyurea.

The polymeric shell may comprise one or more components in addition to the one or more wall-forming polymers. Preferably, the polymeric shell further comprises an emulsifier. In this regard, and as described in more detail below, encapsulation of the liquid core material may be achieved by providing an oil-in-water emulsion in which droplets of an oil (non-aqueous) phase comprising the liquid core material are dispersed in a continuous aqueous phase, and then forming a polymeric shell around the droplets. Such processes are typically performed in the presence of an emulsifier (also known as a stabiliser), which stabilises the emulsion and reduce the likelihood of aggregation of microcapsules during formation of the polymeric shell. Emulsifiers normally stabilise the emulsion by orienting themselves at the oil phase/aqueous phase interface, thus establishing a steric and/or charged boundary layer around each droplet. This layer serves as a barrier to other particles or droplets preventing their intimate contact and coalescence, thereby maintaining a uniform droplet size. Since the emulsifier will typically be retained in the polymeric shell, the polymeric shell of the microcapsules may comprise an emulsifier as an additional component. The emulsifier may be adsorbed on and/or absorbed in the polymeric shell of the microcapsules.

The emulsifier may be a polymer or a surfactant. The emulsifier may be a non-ionic, cationic, anionic, zwitterionic or amphoteric emulsifier. Examples of suitable emulsifiers include, without limitation, cetyl trimethylammonium bromide (CTAB), poly(vinyl alcohol) (PVA), poly(vinyl pyrrolidone) (PVP), poly(acrylic acid) (PAA), poly(methacrylic acid) (PMA), dodecyldimethyl ammonium bromide (DDAB), sodium dodecyl sulfate (SDS) and poly(ethylene glycol). In some examples, the emulsifier is selected from cetyl trimethylammonium bromide, poly(vinyl alcohol) and poly(vinyl pyrrolidone).

The uncoated microcapsules may be formed by emulsifying the liquid core material into droplets and forming a polymeric shell around the droplets. Microencapsulation of the liquid core material can be conducted using a variety of methods known in the art, including coacervation methods, in situ polymerisation methods and interfacial polymerisation methods. Such techniques are known in the art (see, e.g., "Microencapsulation: Methods and Industrial Applications", Edited by Benita and Simon, Marcel Dekker, Inc., 1996; U.S. Pat. No. 2,730,456; U.S. Pat. No. 2,800,457; U.S. Pat. No. 2,800,458; U.S. Pat. No. 4,552,811; U.S. Pat. No. 6,592,990; and U.S. 2006/0263518).

In some examples, the microcapsules are prepared a coacervation method which involves oil-in-water emulsification followed by solvent extraction. Such procedures are known in the art (see, e.g., Loxley et al., Journal of Colloid and Interface Science, vol. 208, pp. 49-62, 1998) and involve the use of a non-aqueous phase comprising a polymeric material that is capable of forming a polymeric shell, a poor solvent for the polymeric material, and a co-solvent which is a good solvent for the polymeric material. The non-aqueous and aqueous phases are emulsified, forming an oil-in-water emulsion comprising droplets of the non-aqueous phase dispersed in the continuous aqueous phase. The co-solvent is then partially or wholly extracted from the non-aqueous phase, causing the polymeric material to precipitate around the poor solvent, thereby encapsulating the poor solvent.

The uncoated microcapsules may be prepared by: (i) providing a non-aqueous phase comprising a polymeric material that is capable of forming a polymeric shell, a liquid core material which is a poor solvent for the polymeric material, and a co-solvent which is a good solvent for the polymeric material; (ii) providing an aqueous phase; (iii) emulsifying the non-aqueous phase and the aqueous phase to form an emulsion comprising droplets of the non-aqueous phase dispersed within the aqueous phase; and (iv) extracting at least a portion of the co-solvent from the non-aqueous phase such that the polymeric material precipitates around droplets comprising the liquid core material, thereby encapsulating the liquid core material.

In some examples, the polymeric material comprises a polyacrylate, e.g. poly(methyl methacrylate) (PMMA), poly(ethyl methacrylate) (PEMA) or a combination thereof. In some examples, the polymeric material consists of poly(methyl methacrylate) (PMMA) or poly(ethyl methacrylate) (PEMA).

Preferably, the polymeric material has a weight average molecular weight of at least 10 kDa, more preferably at least 50 kDa, more preferably at least 100 kDa. Preferably, the polymeric material has a weight average molecular weight of from 10 to 1000 kDa, more preferably from 50 to 800 kDa, more preferably from 100 to 600 kDa.

With regard to the chemical composition of the non-aqueous phase, the liquid core material is preferably present in an amount of from 0.5 to 50%, preferably from 1 to 45%, and more preferably from 3 to 40% by weight of the non-aqueous phase. The polymeric material is preferably present in the non-aqueous phase in an amount of from 0.5 to 15%, preferably from 1 to 10%, and more preferably from 2 to 8% by weight of the non-aqueous phase. The co-solvent is preferably present in an amount of from 40 to 98%, preferably from 50 to 98%, and more preferably from 60 to 95% by weight of the non-aqueous phase. In some examples, the non-aqueous phase consists of the liquid core material, the polymeric material and the co-solvent.

In some examples, the co-solvent is a volatile material, e.g. dichloromethane (DCM), and is extracted from the non-aqueous phase by evaporation. In this case, precipitation of the polymeric material may be aided by heating the emulsion to promote evaporation of the co-solvent. For instance, the method may be carried out at a temperature of at least 30° C.

Preferably, at least one of the aqueous and non-aqueous phases comprises an emulsifier. More preferably, the aqueous phase comprises an emulsifier. Examples of emulsifiers include, without limitation, poly(vinyl alcohol) (PVA), poly(vinyl pyrrolidone) (PVP), cetyl trimethylammonium bromide (CTAB) and mixtures thereof. In some examples, the emulsifier is present in an amount of from 0.01 to 50% by weight of the aqueous phase, preferably from 0.5 to 30%, and more preferably from 0.1 to 10% by weight.

In some examples, the polymeric shell is formed by an interfacial polymerisation process. For example, the polymeric shell may be prepared by an interfacial polymerisation process which involves the use of a non-aqueous phase comprising the liquid core material and one or more oil-soluble monomers; and an aqueous phase comprising one or more water-soluble monomers and an emulsifier. The non-aqueous and aqueous phases are emulsified to form an emulsion comprising droplets of the non-aqueous phase dispersed within the aqueous phase. The monomers are then polymerised, typically by heating, with polymerisation occurring at the interface between the non-aqueous phase and the aqueous phase.

Alternatively, the polymeric shell may be obtainable by interfacial polymerisation of a pre-polymer. Such processes may be used to prepare a range of different polymeric shell materials. For example, a polymeric shell comprising a polyacrylate, polyamine or polyurea material may be prepared by such a process.

Preferably, the polymeric material comprises a polyacrylate. In some examples, the polymeric shell comprises a polyacrylate and is obtainable by interfacial polymerisation of a pre-polymer, wherein the pre-polymer is obtained by reacting a mixture comprising: (i) an aminoalkyl acrylate monomer, an aminoalkyl methacrylate monomer, or a mixture thereof; and (ii) an acrylate monomer, a methacrylate monomer, an acrylate oligomer, a methacrylate oligomer, or a mixture thereof.

More preferably, the polymeric shell is prepared by a process comprising:

(i) providing a non-aqueous phase comprising the liquid core material, an amine monomer, a multifunctional acrylate or methacrylate monomer or oligomer, an acid and a free radical initiator;

(ii) reacting the amine monomer with the multifunctional acrylate or methacrylate monomer or oligomer to form a pre-polymer;

(iii) providing an aqueous phase comprising an emulsifier, an alkali or alkali salt, and optionally a free radical initiator;

(iv) contacting the non-aqueous phase with the aqueous phase under conditions such that an emulsion is formed comprising droplets of the non-aqueous phase dispersed in the aqueous phase; and (v) polymerising the pre-polymer to form a polymeric shell which encapsulates the liquid droplets.

The amine monomer is an oil-soluble or oil-dispersible amine monomer, more preferably an aminoalkyl acrylate or aminoalkyl methacrylate. In some examples, the amine monomer is selected from aminoalkyl acrylates, alkyl aminoalkyl acrylates, dialkyl aminoalkyl acrylates, aminoalkyl methacrylates, alkylamino aminoalkyl methacrylates, dialkyl aminoalkyl methacrylates, tertiarybutyl aminoethyl methacrylates, diethylaminoethyl methacrylates, dimethylaminoethyl methacrylates, dipropylaminoethyl methacrylates, and mixtures thereof. Preferred amine monomers are diethylaminoethyl methacrylate, dimethylaminoethyl methacrylate, tert-butyl aminoethyl methacrylate, and mixtures thereof. More preferably, the amine is tert-butylaminoethyl methacrylate and the multifunctional acrylate or methacrylate monomer or oligomer is a hexafunctional aromatic urethane acrylate oligomer.

In the above process, an aqueous phase comprising an emulsifer and an alkali or alkali salt is used. Examples of emulsifiers include, without limitation, poly(vinyl alcohol) (PVA), poly(vinyl pyrrolidone) (PVP), cetyl trimethylammonium bromide (CTAB), and mixtures thereof. In some examples, the alkali or alkali salt is sodium hydroxide.

The interfacial polymerisation process is preferably performed in the presence of a free radical initiator. Examples of suitable free radical initiators include azo initiators, peroxide, alkyl peroxides, dialkyl peroxides, peroxyesters, peroxycarbonates, peroxyketones and peroxydicarbonates. In some examples, the free radical initiator is selected from 2,2'-azobis-(2,4-dimethylpentanenitrile), 2,2'-azobis-(2-methyl-butyronitrile), and mixtures thereof. A free radical initiator may be present in the aqueous phase, the non-aqueous phase, or both.

In some examples, the microcapsules are prepared by an in situ polymerisation process. Such processes are known in the art and generally involve preparing an emulsion comprising droplets of the liquid core material dispersed in a continuous phase comprising a precursor material which can be polymerised to form a polymeric shell; and polymerising the precursor material to form a polymeric shell, thereby encapsulating the liquid droplets. The polymerisation process is similar to that of interfacial polymerisation processes, except in that no precursor materials for the polymeric shell are included in the liquid core material in in situ polymerisation processes. Thus, polymerisation occurs solely in the continuous phase, rather than on either side of the interface between the continuous phase and the core material.

Examples of precursor materials for the polymeric shell include, without limitation, pre-polymer resins such as urea resins, melamine resins, acrylate esters, and isocyanate resins. Preferably, the polymeric shell is formed by the polymerisation of a precursor material selected from: melamine-formaldehyde resins; urea-formaldehyde resins; monomeric or low molecular weight polymers of methylol melamine; monomeric or low molecular weight polymers of dimethylol urea or methylated dimethylol urea; and partially methylated methylol melamine.

The use of melamine-formaldehyde resins or urea-formaldehyde resins as the precursor material is particularly preferred. Procedures for preparing microcapsules comprising from such precursor materials are known in the art (see, e.g., U.S. Pat. No. 3,516,941, U.S. Pat. No. 5,066,419 and U.S. Pat. No. 5,154,842). The capsules are made by first emulsifying the liquid core material as small droplets in an aqueous phase comprising the melamine-formaldehyde or urea-formaldehyde resin, and then allowing the polymerisation reaction to proceed along with precipitation at the oil-water interface.

In some examples, the microcapsules may be prepared by a process comprising:

(i) providing a non-aqueous phase comprising the liquid core material;

(ii) providing an aqueous phase comprising a melamine-formaldehyde pre-polymer (e.g. a partially methylated methylol melamine resin);

(iii) emulsifying the non-aqueous and aqueous phases to form an emulsion comprising droplets of the non-aqueous phase dispersed in the aqueous phase; and (iv) condensing the melamine-formaldehyde pre-polymer, thereby forming a melamine-formaldehyde polymer which precipitates from the aqueous phase and encapsulates said droplets.

The polymerisation process is preferably performed using an emulsifier, which is preferably present in the aqueous phase. By way of illustration, an anionic emulsifier (e.g. copolymers of butyl acrylate and acrylic acid) and/or a neutral emulsifier (e.g. PVP) may be used.

Condensation of the melamine-formaldehyde pre-polymer may be initiated by, e.g., lowering the pH of the emulsion. The pH of the emulsion may be adjusted using a base as appropriate. Examples of suitable bases include alkali metal hydroxides (e.g. sodium hydroxide), ammonia, and triethanolamine.

In each of the emulsification processes described herein, emulsification can be conducted using any suitable mixing device known in the art. For example, a homogeniser, colloid mill, ultrasonic dispersion device, or ultrasonic emulsifier may be used. Preferably, a homogeniser is used.

The resulting polymeric shell may have a thickness of greater than 0.5 nm, preferably greater than 1 nm, and more preferably greater than 2 nm. Typically, the polymeric shell will have a shell thickness of less than 2000 nm, preferably less than 1500 nm, and more preferably less than 1100 nm. The microcapsules preferably have a polymeric shell with a thickness of from 1 to 2000 nm, such as from 2 to 1100 nm. Factors such as the concentration of the shell-forming material in the emulsion will dictate the thickness of the polymeric shell.

The size of the microcapsules can be controlled by altering factors such as the stirring speed and the shape of the stirring blade or rotor blade of the stirrer or homomixer used during the emulsification step of the microencapsulation process, or by adjusting the reaction rate by altering the polymerisation conditions (e.g. the reaction temperature and time) for the polymeric material. In particular, the size of the microcapsules may be controlled by regulating the stirring speed, which in turn regulates the size of the droplets of the liquid core material in the emulsion.

Metallic Coating

The coated microcapsules may further comprise a metallic coating which surrounds the microcapsules. The metallic coating has a maximum thickness of 1000 nm and comprises particles of a first metal adsorbed on the polymeric shell and a film of a second metal disposed on said particles. The film of the second metal provides for a continuous coating which surrounds the surface of the microcapsule. Preferably the thickness of the metallic coating is substantially uniform throughout the coating.

The particles of the first metal are preferably nanoparticles. The term "nanoparticles" as used herein refers to particles having a particle size of from 1 to 200 nm. Preferably, the metal nanoparticles have a particle size of less than 100 nm, e.g. less than 50 nm. More preferably, the metal nanoparticles have a particle size of less than 10 nm, more preferably less than 5 nm, and more preferably less than 3 nm. In this regard, the use of smaller metal nanoparticles may result in the formation of a thinner metallic coating. The nanoparticles will typically have a spheroidal geometry, but they may exist in more complex forms such as rods, stars, ellipsoids, cubes or sheets.

In some examples, the nanoparticles comprise gold, silver, copper, tin, cobalt, tungsten, platinum, palladium, nickel, iron or aluminium nanoparticles, or mixtures thereof. In some examples, the nanoparticles comprise an alloy of two or more metals, e.g. an alloy of two or more metals selected from gold, silver, copper, tin, cobalt, tungsten, platinum, palladium, nickel, iron and aluminium. In some examples, the nanoparticles comprise a metal oxide, e.g. aluminium oxide or an iron oxide. In some examples, the nanoparticles comprise core-shell particles comprising a core of a first metal or metal oxide surrounded by a shell of a second metal or metal oxide. In some examples, the nanoparticles consist of a single metal.

As described in more detail below, the film of the second metal is preferably applied by an electroless plating procedure which is catalysed by the particles of the first metal. It is therefore preferred that the particles of the first metal comprise a metal which catalyses the electroless plating process.

The first metal may be selected from the transition metals and p-block metals, e.g. a metal selected from those metals listed in Groups 9 to 14 of the Periodic Table, in particular a metal selected from Groups 10, 11 and 14. Preferably, the first metal is a metal selected from nickel, palladium, platinum, silver, gold, tin and combinations thereof. Preferably, the first metal comprises platinum, silver, gold, or a mixture thereof.

The first and second metals may be the same or different. Preferably, the second metal is different to the first metal.

The second metal is preferably a metal that is capable of being deposited via an electroless plating process. The second metal may be a transition metal, e.g. a metal selected from those metals listed in Groups 9 to 14 of the Periodic Table, in particular a metal selected from Groups 10 and 11. Preferably, the second metal is a metal selected from silver, gold, copper and combinations thereof.

In some examples, the first metal is selected from Au, Pt, Pd, Sn, Ag and combinations thereof; and the second metal is selected from Au, Ag, Cu, Ni and combinations thereof.

In some examples, the first metal is selected from Au, Pt, Pd, Sn, Ag and combinations thereof (e.g. Sn/Ag) and the second metal is Au. In some examples, the first metal is selected from Sn, Pt, Ag, Au and combinations thereof (e.g. Pt/Sn) and the second metal is Ag. In some examples, the first metal is selected from Sn, Ag, Ni and combinations thereof (e.g. Sn/Ni or Sn/Ag) and the second metal is Cu. In some examples, the first metal is selected from Sn, Pd, Ag and combinations thereof (e.g. Sn/Pd) and the second metal is Ni.

In some examples, the first metal is Pt and the second metal is Au; the first metal is Au and the second metal is Ag; or the first metal is Au and the second metal is Cu. More preferably, the first metal is Au and the second metal is Ag; or the first metal is Pt and the second metal is Au.

The particles of the first metal are preferably adsorbed onto the polymeric shell in the form of a discontinuous layer such that, prior to application of the metallic film, the surface of the polymeric shell comprises regions comprising adsorbed metal particles and regions in which adsorbed metal particles are absent. The metal particles may be distributed over the surface of the polymeric shell in a substantially uniform manner.

The thickness of the film of the second metal may vary with the density of the particles of the first metal that are adsorbed onto the polymeric shell of the microcapsule, with a higher density of particles of the first metal typically encouraging the growth of a thinner film. In some examples, the particles are deposited onto the polymeric shell at a density such that said particles cover from 0.1 to 80% of the surface area of the polymeric shell, e.g. from 0.5 to 40% of the surface area of the polymeric shell, e.g. from 1 to 4% of the surface area of the polymeric shell. The density of the particles on the polymeric shell may be determined using the procedure described in the Test Methods section herein.

The particles of the first metal are preferably adsorbed onto the polymeric shell by: (i) adsorbing charge-stabilised nanoparticles of the first metal onto the polymeric shell; (ii) adsorbing sterically-stabilised nanoparticles of the first metal onto the polymeric shell; or (iii) adsorbing particles of the first metal which are formed by reduction in situ. These methods are described in more detail below.

Deposition of the First Metal: Adsorption of Charge-Stabilised Nanoparticles

In some examples, the particles of the first metal are charge-stabilised nanoparticles which are adsorbed on the polymeric shell. Charge-stabilised nanoparticles are nanoparticles which comprise a charged species adsorbed on the surface thereof. Since the stabiliser is a charged species, it will impart a charged surface to the nanoparticles which can be exploited in order to adsorb the metal particles to the surface of the polymeric shell. In some examples, the particles of the first metal are adsorbed on the polymeric shell by electrostatic interaction.

The particles are preferably adsorbed on a surface-modifying agent that forms part of the polymeric shell. The surface-modifying agent may be adsorbed on and/or absorbed within the polymeric shell. Preferably, the polymeric shell was obtained by an emulsification process in which the surface-modifying agent was employed as an emulsifier, with the emulsifier being retained in the resulting shell. The surface-modifying agent preferably presents a charged surface which is used to electrostatically attract and adsorb the charge-stabilised nanoparticles on to the polymeric shell.

In some examples, the particles of the first metal are charge-stabilised by an anionic stabiliser. In some examples, the anionic stabiliser is selected from borohydride anions and citrate anions. In some examples, the anionic stabiliser is an anionic surfactant, e.g. an anionic surfactant selected from sodium dodecyl sulfate, sodium laureth sulfate, dodecyl benzene sulfonic acid, perfluorooctanesulfonate, dioctyl sodium sulfosuccinate and sodium stearate. Preferably, the particles are borohydride-stabilised or citrate-stabilised nanoparticles.

In some examples, the particles of the first metal have a zeta potential of from −20 mV to −150 mV, e.g. from −30 mV to −90 mV.

Where the particles of the first metal are stabilised by an anionic stabiliser, it is preferable for the surface of the polymeric shell to be neutral or cationic. In some examples, the polymeric shell has a substantially neutral surface having a zeta potential of from −10 mV to +10 mV, e.g. from −5 mV to +5 mV. In some examples, the polymeric shell has a positively charged surface, e.g. having a zeta potential of from +20 mV to +150 mV, e.g. from +30 mV to +90 mV.

In some examples, the particles of the first metal are stabilised by an anionic stabiliser and the polymeric shell comprises a non-ionic surface-modifying agent. In some examples, the surface-modifying agent is a non-ionic polymer, e.g. a non-ionic polymer selected from poly(vinyl alcohol) and poly(vinyl pyrrolidone).

In some examples, the particles of the first metal are stabilised by an anionic stabiliser and the polymeric shell comprises a cationic surface-modifying agent. The surface-modifying agent may be a cationic surfactant or a cationic polymer. Examples of cationic surfactants include, without limitation, alkyl ammonium surfactants such as cetyl trimethylammonium bromide, dodecyl dimethylammonium bromide, cetyl trimethylammonium chloride, benzalkonium chloride, cetylpyridinium chloride, dioctadecyl dimethylammonium chloride and dioctadecyl dimethylammonium bromide. Examples of cationic polymers include, without limitation, poly(diethylaminoethyl methacrylate), poly(dimethylaminoethyl methacrylate), poly(tertiarybutylaminoethyl methacrylate) and di-block copolymers formed of a first block comprising a poly(aminoalkyl acrylate) and a second block comprising a poly(alkyl acrylate). More preferably, the surface-modifying agent is cetyl trimethylammonium bromide.

Alternatively, the particles of the first metal may be charge-stabilised by a cationic stabiliser. Examples of cationic stabilisers include cationic surfactants such as quaternary ammonium surfactants, e.g. cetyl trimethylammonium bromide, tetraoctylammonium bromide and dodecyl trimethylammonium bromide. Other quaternary ammonium surfactants include the esterquats, i.e. quaternary ammonium surfactants containing an ester group.

In some examples, the particles of the first metal have a zeta potential of from +20 mV to +150 mV, e.g. from +30 mV to +90 mV.

Where the particles of the first metal are stabilised by a cationic stabiliser, it is preferable for the surface of the polymeric shell to be neutral or anionic. In some examples, the polymeric shell has a substantially neutral surface having a zeta potential of from −10 mV to +10 mV, e.g. from −5 mV to +5 mV. In some examples, the polymeric shell has a positively charged surface, e.g. having a zeta potential of from −20 mV to −150 mV, e.g. from −30 mV to −90 mV.

In some examples, the particles of the first metal are stabilised by a cationic stabiliser and the polymeric shell comprises a non-ionic surface-modifying agent. In some examples, the surface-modifying agent is a non-ionic polymer, e.g. a non-ionic polymer selected from poly(vinyl alcohol) and poly(vinylpyrrolidone).

In some examples, the particles of the first metal are stabilised by a cationic stabiliser and the polymeric shell comprises an anionic surface-modifying agent. The surface-modifying agent may be an anionic surfactant or an anionic polymer. Examples of anionic surfactants include, without limitation, sodium dodecyl sulfate, sodium laureth sulfate, dodecyl benzene sulfonic acid, dioctyl sodium sulfosuccinate, perfluorooctanesulfonate, dioctyl sodium sulfosuccinate and sodium stearate. Examples of anionic polymers include, without limitation, polyacids such as poly(acrylic acid) and poly(methacrylic acid).

The particles of the first metal may alternatively be charge-stabilised by a zwitterionic stabiliser. In some examples, the zwitterionic stabiliser is a zwitterionic surfactant. Examples of zwitterionic surfactants include aminobetaines, imidazoline derivatives and phospholipids, e.g. phosphatidyl cholines.

The charge-stabilised nanoparticles may be prepared using suitable procedures known in the art (see, e.g., G. Frens, Nature, 1973, 241, 20-22). Such procedures will typically involve reducing metal ions in solution in the presence of charged stabiliser. Thus, the charge-stabilised nanoparticles may be obtained by providing a solution comprising ions of the first metal and a charged stabiliser, and reducing the ions to form metal particles which are charge-stabilised by the stabiliser.

In some examples, metal ions in solution are reduced by a reducing agent which becomes the charged stabiliser e.g. by sodium borohydride or by sodium citrate. By way of illustration, and without limitation, borohydride-stabilised gold nanoparticles may be prepared by contacting an aqueous solution of chloroauric acid with sodium borohydride.

The resulting charge-stabilised nanoparticles may then be contacted with uncoated microcapsules under appropriate conditions, e.g. at ambient temperature. The microcapsules may then be washed to remove any unbound particles.

Preferably, the ions of the first metal are present in the solution at a concentration of from 0.005 to 50 mM, e.g. from 0.01 to 20 mM, e.g. from 0.05 to 5 mM. Preferably, the charged stabiliser is present in the solution at a concentration of from 0.005 to 50 mM, e.g. from 0.01 to 20 mM, e.g. from 0.05 to 5 mM.

Deposition of the First Metal: Adsorption of Sterically-Stabilised Nanoparticles In some examples, the first metal is deposited by adsorbing sterically-stabilised nanoparticles of the first metal onto the surface of the polymeric shell. Sterically-stabilised nanoparticles generally comprise a polymer or other macromolecule which is adsorbed on the surface of the metal particles, forming a protective sheath around the particles and minimising aggregation. The size of the steric stabiliser can be exploited in order to adsorb the metal particles onto the surface of the polymeric shell. In some examples, the particles of the first metal are adsorbed on the polymeric shell by steric interaction.

In some examples, the nanoparticles are sterically-stabilised by a polymeric stabiliser. Preferably, the polymer comprises one or more groups selected from carboxyl, hydroxyl, amine, and ester groups. The polymer may be a homopolymer or a copolymer (e.g. a graft copolymer or a block copolymer). Examples of suitable polymers include poly(ethylene oxide), polyethylene glycol, poly(acrylic acid), poly(acrylamide), poly(ethylene imine), poly(vinyl alcohol), carboxymethyl cellulose, chitosan, guar gum, gelatin, amylose, amylopectin, and sodium alginate.

Preferably the polymeric stabiliser has a weight average molecular weight of at least 5 kDa, more preferably at least 10 kDa, more preferably at least 20 kDa. Preferably, the molecular weight of the polymeric stabiliser is from 5 to 100 kDa, more preferably from 10 to 80 kDa, more preferably from 20 to 40 kDa.

In some examples, the polymeric stabiliser is a non-ionic polymer. Examples of non-ionic polymers include, without limitation, poly(vinyl alcohol), poly(vinyl propylene), poly(ethylene glycol) and poly(vinyl pyrrolidone). Poly(vinyl pyrrolidone) is particularly preferred as a steric stabiliser.

In some examples, the polymeric stabiliser is a cationic polymer. Examples of cationic polymers include, without limitation, poly(allyl amine) polymers, e.g. poly(allyl amine) hydrochloride).

In some examples, the polymeric stabiliser is an anionic polymer. Examples of anionic polymers include, without limitation, polyacids, e.g. poly(acrylic acid) or poly(methacrylic acid).

In some examples, the nanoparticles are sterically-stabilised by a polymeric surfactant. Examples of suitable surfactants include, without limitation, polyoxyalkylene glycol alkyl ethers (e.g. polyoxyethylene glycol alkyl ethers and polyoxypropylene glycol alkyl ethers), sorbitan esters (e.g. polysorbates), fatty acid esters, poly(isobutenyl) succinic anhydride amine derivatives and amine oxides.

As with the polymeric stabiliser, the polymeric surfactant preferably has a weight average molecular weight of at least 5 kDa, more preferably at least 10 kDa, more preferably at least 20 kDa. Preferably, the polymeric surfactant has a weight average molecular weight of from 5 to 100 kDa, more preferably from 10 to 80 kDa, more preferably from 20 to 40 kDa.

The particles are preferably adsorbed on a surface-modifying agent that forms part of the polymeric shell. The surface-modifying agent may be adsorbed on and/or absorbed within the polymeric shell. Preferably, the polymeric shell was obtained by an emulsification process in which the surface-modifying agent was employed as an emulsifier, with the emulsifier being retained in the resulting shell. The sterically-stabilised nanoparticles preferably bind via steric interactions to the surface-modifying agent.

In some examples, the surface-modifying agent is a non-ionic surface-modifying agent, e.g. a non-ionic surfactant or a non-ionic polymer. Examples of non-ionic polymers include, without limitation, poly(vinyl alcohol) and poly(vinyl pyrrolidone). More preferably, the non-ionic polymer is poly(vinyl alcohol).

In some examples, the surface-modifying agent is a cationic surface-modifying agent, e.g. a cationic surfactant or a cationic polymer. Examples of cationic surfactants include, without limitation, cetyl trimethylammonium bromide, dodecyl dimethylammonium bromide, cetyl trimethylammonium chloride, benzalkonium chloride, cetylpyridinium chloride, dioctadecyl dimethylammonium chloride and dioctadecyl dimethylammonium bromide. Preferably, the cationic surface-modifying agent is cetyl trimethylammonium bromide.

In some examples, the surface-modifying agent is an anionic surface-modifying agent, e.g. an anionic surfactant or an anionic polymer. Examples of anionic surfactants include, without limitation, sodium dodecyl sulfate, sodium laureth sulfate, dodecyl benzene sulfonic acid, dioctyl sodium sulfosuccinate, perfluorooctanesulfonate, dioctyl sodium sulfosuccinate and sodium stearate. Examples of anionic polymers include, without limitation, polyacids such as poly(acrylic acid) and poly(methacrylic acid).

Suitable procedures for preparing the sterically-stabilised nanoparticles are known in the art (see, e.g., Horiuchi et al., Surface and Coatings Technology, 2010, 204, 3811-3817). By way of illustration, sterically-stabilised nanoparticles may be prepared by reducing metal ions in solution in the presence of a stabiliser.

Thus, in some examples, the sterically-stabilised nanoparticles are obtained by providing a solution comprising ions of the first metal and a stabiliser, and reducing the ions to form metal particles which are sterically-stabilised by the stabiliser. Preferably, the ions of the first metal are present in the solution at a concentration of from 0.01 to 100 mM, e.g. from 0.05 to 50 mM, e.g. from 0.1 to 10 mM. Preferably, the stabiliser is present in the solution at a concentration of from 0.0001 to 1 mM, e.g. from 0.005 to 0.5 mM, e.g. from 0.001 to 0.1 mM.

The particles of the first metal may be adsorbed on to the polymeric shell of the microcapsule by contacting the microcapsule with a slurry comprising said particles. Preferably, the metal nanoparticles are present in the slurry in an amount of more than 0.2% by weight and the slurry comprises less than 0.01% by weight of unbound stabiliser.

The contacting may take place under ambient conditions. However, in order to facilitate adsorption of the particles onto the microcapsule surface, the microcapsules may be heated so as to enhance penetration of the sterically-stabilised particles within the polymeric shell. Preferably, the microcapsules are heated to a temperature of from 30° C. to 80° C., e.g. from 40° C. to 70° C. In some examples, the polymeric shell comprises an amorphous polymer and the microcapsule is heated to a temperature above standard ambient temperature but below the glass transition temperature ($T_g$) of the polymer. Preferably, the elevated temperature is no more than 30° C. below, e.g. no more than 20° C. below, the glass transition temperature of the amorphous polymer. Examples of amorphous polymers include, without limitation, polyacrylates, e.g. poly(methyl methacrylate) and poly(ethyl methacrylate). The glass transition temperature of the polymer may be determined by differential scanning calorimetry (DSC) following ASTM E1356 ("Standard Test Method for Assignment of the Glass Transition Temperature by Differential Scanning calorimetry").

Deposition of the First Metal: Deposition by Reduction In Situ

In some examples, the particles of the first metal are adsorbed on to the polymeric shell by contacting the uncoated microcapsule with a solution comprising ions of the first metal and a reducing agent. The presence of the reducing agent causes the ions of the first metal to be reduced in situ. As the metal ions are reduced, they precipitate from the solution as metal particles and seek to lower the energy of the system by adsorbing onto the polymeric shell of the microcapsule. The first metal may also be adsorbed onto the polymeric shell of the microcapsule during the deposition process in the form of ions which have not been reduced by the reducing agent.

The reducing agent that is contacted with the uncoated microcapsule is preferably in solution. More preferably, the reducing agent is added to a solution comprising the metal ions and the uncoated microcapsule. Thus, deposition of the metal particles on the microcapsule surface may be achieved by preparing an aqueous solution comprising ions of the first metal and uncoated microcapsules. A reducing agent is then added to the solution, resulting in reduction of the metal ions and the precipitation of particles of the first metal onto the surface of the microcapsules. The reaction is allowed to progress for a time sufficient to allow the desired deposition of the metal particles on the microcapsule surface. The capsules may then be washed, separated from the other reagents and redispersed in water. The deposition process may be carried out at room temperature.

Preferably, the ions of the first metal are present in the solution at a concentration of from 0.005 to 50 mM, e.g. from 0.01 to 20 mM, e.g. from 0.05 to 5 mM. Preferably, the reducing agent is present in the solution at a concentration of from 0.05 to 500 mM, e.g. from 0.1 to 200 mM, e.g. from 0.5 to 50 mM.

The particles are preferably adsorbed on a surface-modifying agent that is present in the polymeric shell. The surface-modifying agent may be adsorbed on and/or absorbed within the polymeric shell. Preferably, the polymeric shell was obtained by an emulsification process in which the surface-modifying agent was employed as an emulsifier, with the emulsifier being retained in the resulting shell. The particles of the first metal may be adsorbed to the polymeric shell by one or more interactions selected from steric interactions and electrostatic interactions.

In some examples, the surface-modifying agent is a non-ionic surface-modifying agent, e.g. a non-ionic polymer. Examples of non-ionic polymers include, without limitation, poly(vinyl alcohol) and poly(vinyl pyrrolidone). More preferably, the non-ionic polymer is poly(vinyl alcohol).

In some examples, the surface-modifying agent is a cationic surface-modifying agent, e.g. a cationic surfactant or a cationic polymer. Examples of cationic surfactants include, without limitation, cetyl trimethylammonium bromide, dodecyl dimethylammonium bromide, cetyl trimethylammonium chloride, benzalkonium chloride, cetylpyridinium chloride, dioctadecyl dimethylammonium chloride and dioctadecyl dimethylammonium bromide. Preferably, the surface-modifying agent is cetyl trimethylammonium bromide.

In some examples, the surface-modifying agent is an anionic surface-modifying agent, e.g. an anionic surfactant or an anionic polymer. Examples of anionic surfactants include, without limitation, sodium dodecyl sulfate, sodium laureth sulfate, dodecyl benzene sulfonic acid, dioctyl sodium sulfosuccinate, perfluorooctanesulfonate, dioctyl sodium sulfosuccinate and sodium stearate. Examples of anionic polymers include, without limitation, polyacids such as poly(acrylic acid) and poly(methacrylic acid).

Deposition of the Second Metal

Once the particles of the first metal have been adsorbed onto the polymeric shell, a film of a second metal is formed on the particles of the first metal, thereby coating the polymeric shell with a continuous metallic film that surrounds the microcapsule. Preferably the thickness of the metallic coating is substantially uniform throughout the coating.

The metallic film is preferably formed by an electroless plating process in which the deposition of the second metal is catalysed by the adsorbed particles of the first metal. The electroless deposition process will generally comprise contacting microcapsules onto which particles of the first metal have been deposited with a solution of ions of the second metal in the presence of a reducing agent, in the absence of an electric current. The reducing agent is typically a mild reducing agent such as formaldehyde and the electroless plating is preferably performed under alkaline conditions. Once the electroplating reaction commences, the deposition of the metallic coating may become autocatalytic. The thickness of the metallic film may be controlled by limiting the concentration of the ions of the second metal in solution and/or the duration of the electroless plating procedure.

Suitable techniques for conducting the electroless plating procedure are described, for example, in the following documents: Basarir et al., ACS Applied Materials & Interfaces, 2012, 4(3), 1324-1329; Blake et al., Langmuir, 2010, 26(3), 1533-1538; Chen et al., Journal of Physical Chemistry C, 2008, 112(24), 8870-8874; Fujiwara et al., Journal of the Electrochemical Society, 2010, 157(4), pp. D211-D216; Guo et al., Journal of Applied Polymer Science, 2013, 127(5), 4186-4193; Haag et al., Surface and Coatings Technology, 2006, 201(6), 2166-2173; Horiuchi et al., Surface & Coatings Technology, 2010, 204(23), 3811-3817; Ko et al., Journal of the Electrochemical Society, 2010, 157(1), pp. D46-D49; Lin et al., International Journal of Hydrogen Energy, 2010, 35(14), 7555-7562; Liu et al., Langmuir, 2005, 21(5), 1683-1686; Ma et al., Applied Surface Science, 2012, 258(19), 7774-7780; Miyoshi et al., Colloids and Surfaces A: Physicochemical and Engineering Aspects, 2008, 321(1-3), 238-243; Moon et al., 2008, Ultramicroscopy, 108(10), 1307-1310; Wu et al., Journal of Colloid and Interface Science, 2009, 330(2), 359-366; Ye et al., Materials Letters, 2008, 62(4-5), 666-669; and Zhu et al., Surface and Coatings Technology, 2011, 205(8-9), 2985-2988.

By way of illustration, and without limitation, a silver film may be prepared by forming a dispersion comprising silver nitrate, formaldehyde, ammonia and microcapsules comprising particles of the first metal. The dispersion is then stirred for a sufficient period of time until a metallic film of the desired thickness is obtained. The capsules may then be washed, e.g. by centrifugation, in order to separate them from the plating solution.

The ions of the second metal are preferably present in the solution at a concentration of from 0.05 to 2000 mM, e.g. from 0.1 to 1750 mM, e.g. from 0.5 to 1500 mM. Preferably, the reducing agent is present in the solution at a concentration of from 0.05 to 3500 mM, e.g. from 0.1 to 3000 mM, e.g. from 0.5 to 2500 mM. Preferably, the second metal and the reducing agent are present in the solution at a molar ratio of second metal to reducing agent of from 1:10 to 4:1, e.g. from 1:5 to 2:1, e.g. from 1:3 to 1:1.

The electroless plating process may be performed at any suitable temperature, e.g. a temperature of from 0 to 80° C. Preferably, the electroless plating process is performed at room temperature.

Characteristics and Properties of the Coated Microcapsules

The coated microcapsules may be obtained in a range of different particle sizes. Preferably, the coated microcapsules have a particle size of at least 0.1 microns, more preferably at least 1 micron. Typically, the coated microcapsules will have particle size of 500 microns or less, such as 100 microns or less, and more preferably 50 microns or less. Preferably, the coated microcapsules have a particle size of from 0.1 to 500 microns, e.g. from 1 to 100 microns, e.g. from 1 to 30 microns, e.g. from 1 to 20 microns. The particle size of the coated and uncoated microcapsules may be determined using the test procedure described in the Test Methods section herein.

The coated microcapsules comprise a metallic coating having a maximum thickness of 1000 nm. The thickness of the metallic coating may be chosen such that the coated microcapsules rupture and release the encapsulated liquid core material under particular conditions, e.g. under particular stresses. For instance, when the coated microcapsules comprise a perfume oil and form part of a fragrance formulation that is worn by a user, the metallic coating may rupture during use, e.g. due to rubbing of the skin to which the formulation has been applied. In this way, the perfume oil may be released in a controlled manner so that it is perceptible to the user for a prolonged period of time.

Conversely, it is also desirable for the metallic coating to have a minimum thickness so as to reduce the likelihood of solvents permeating through the microcapsule wall and/or the metallic coating rupturing prematurely when the coated microcapsules are stored, transported or used. This is particularly important in the case of fine fragrance formulations, which will typically comprise a polar solvent such as ethanol in which the microcapsules are dispersed.

In some examples, the metallic coating has a maximum thickness of 500 nm, e.g. a maximum thickness of 400 nm, e.g. a maximum thickness of 300 nm, e.g. a maximum thickness of 200 nm, e.g. a maximum thickness of 150 nm, e.g. a maximum thickness of 100 nm, e.g. a maximum thickness of 50 nm. In some examples, the metallic coating has a minimum thickness of 1 nm, e.g. a minimum thickness of 10 nm, e.g. a minimum thickness of 30 nm. In some examples, the metallic coating has: a minimum thickness of 1 nm and a maximum thickness of 500 nm; a minimum thickness of 10 nm and a maximum thickness of 300 nm; or a minimum thickness of 10 nm and a maximum thickness of 200 nm. Preferably, the metallic coating has: a minimum thickness of 10 nm and a maximum thickness of 150 nm; a minimum thickness of 10 nm and a maximum thickness of 100 nm; a minimum thickness of 20 nm and a maximum thickness of 100 nm.

The coated microcapsules are designed to release their liquid core material when the microcapsules are ruptured. The rupture can be caused by forces applied to the shell during mechanical interactions. The microcapsules may have a fracture strength of from about 0.1 MPa to about 25 MPa. The microcapsules preferably have a fracture strength of at least 0.5 MPa. So that the microcapsules are readily friable, they preferably have a fracture strength of less than 25 MPa, more preferably of less than 20 MPa, more preferably of less than 15 MPa. For instance, the microcapsules may have a fracture strength of from 0.5 to 10 MPa. The fracture strength of the microcapsules may be measured according to the Fracture Strength Test Method described in WO 2014/047496 (see pages 28-30 thereof).

The coated microcapsules may be characterised in terms of their permeability. A coated microcapsule may retain more than 50% by weight of the liquid core material under the Ethanol Stability Test described herein. More preferably, the coated microcapsule preferably retains more than 70% by weight of the liquid core material, e.g. more than 80% by weight, e.g. more than 85% by weight, e.g. more than 90% by weight, e.g. more than 95% by weight, e.g. more than 98% by weight, when tested under the Ethanol Stability Leakage Test described herein.

In some examples, the metallic coating is applied to an uncoated microcapsule which would otherwise retain less than 20% by weight of its liquid core material when tested under the Ethanol Stability Leakage Test described herein, e.g. less than 10%, e.g. less than 5%, e.g. less than 1%.

Compositions/Articles

The coated microcapsules may be included in compositions (i.e. products intended to be sold to consumers without further modification or processing). In some examples, the compositions may include from 0.001% to 99%, by weight of the composition of the coated microcapsules, alternatively from 0.01% to 90% by weight of the composition of the coated microcapsules, alternatively from 0.1% to 75% by weight of the composition of the coated microcapsules, alternatively from 0.1% to 25% by weight of the composition of the coated microcapsules, alternatively from 1% to 15% by weight of the composition of the coated microcapsules. The composition may include a mixture of different coated microcapsules of the present disclosure, the mixture comprising a plurality of coated microcapsules comprising a first liquid core material and a plurality of coated microcapsules comprising a second liquid core material. Alternatively or additionally, the composition may comprise other microcapsules, e.g. uncoated microcapsules, in addition to the coated microcapsules disclosed herein.

In some examples, at least 75%, 85% or even 90% by weight of the coated microcapsules in the composition have a particle size of from 1 microns to 100 microns, more preferably from 1 microns to 50 microns, even more preferably from 10 microns to 50 microns, most preferably from 1 microns to 30 microns. Preferably, at least 75%, 85% or even 90% by weight of the coated microcapsules have a polymeric shell thickness of from 60 nm to 250 nm, more preferably from 80 nm to 180 nm, even more preferably from 100 nm to 160 nm.

In some examples, the compositions are incorporated into consumer products (i.e. products intended to be sold to consumers without further modification or processing). Moreover, coated microcapsules may be applied to any article, such as a fabric or any absorbent material including, but not limited to, feminine hygiene products, diapers, and adult incontinence products. The composition may also be included in an article, non-limiting examples of which include a dispenser/container. The compositions/articles disclosed herein may be made by combining the coated microcapsules disclosed herein with the desired adjunct material to form the consumer product. The microcapsules may be combined with the adjuncts material when the microcapsules are in one or more forms, including a slurry form, neat particle form, and spray dried particle form. The microcapsules may be combined with the adjuncts material by methods that include mixing and/or spraying. The coated microcapsules may be formulated into any suitable form and prepared by any process chosen by the formulator, non-limiting examples of which are described in U.S. Pat. No. 5,879,584 which is incorporated herein by reference.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Non-limiting examples of consumer products useful herein include products for treating hair (human, dog, and/or cat), including, bleaching, coloring, dyeing, conditioning, growing, removing, retarding growth, shampooing, styling; deodorants and antiperspirants; personal cleansing; color cosmetics; products, and/or methods relating to treating skin (human, dog, and/or cat), including application of creams, lotions, and other topically applied products for consumer use; and products and/or methods relating to orally administered materials for enhancing the appearance of hair, skin, and/or nails (human, dog, and/or cat); shaving; body sprays; and fine fragrances like colognes and perfumes; products for treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products relating to disposable absorbent and/or non-absorbent articles including adult incontinence garments, bibs, diapers, training pants, infant and toddler care wipes; hand soaps, shampoos, lotions, oral care implements (non-limiting examples including toothpaste, mouth wash, and tooth whitening agents like Crest® Whitestrips®), and clothing; products such as wet or dry bath tissue, facial tissue, disposable handkerchiefs, disposable towels, and/or wipes; products relating to catamenial pads, incontinence pads, interlabial pads, panty liners, pessaries, sanitary napkins, tampons and tampon applicators, and/or wipes.

Personal Care Compositions

In some examples, the consumer product may be a personal care composition, that is, a composition intended to be applied anywhere on the human body and/or articles of clothing for any period of time. Non-limiting examples of personal care compositions include products such as those intended to treat and/or clean hair, styling products, deodorants and antiperspirants, personal cleansing products, cosmetics products, product relating to treating skin such as creams, lotions, and other topically applied products for consumer use; shaving products; hair colouring/bleaching products; body sprays; and fine fragrances like colognes and perfumes. The personal care compositions may be manufactured by any method known in the art and packaged in any dispenser known in the art. In some examples, the personal care composition may include the coated microcapsules and one or more adjunct materials. In some examples, the personal care compositions include the coated microcapsules and one or more adjunct materials, wherein the coated microcapsules comprise at least one perfume oil. In some examples, the personal care composition may include from about 0.01% to about 20%, by weight of the personal care composition, of microcapsules. Some non-limiting examples of personal care compositions are described in further detail below.

Shampoo Composition

The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %. The shampoo composition may also comprise a shampoo gel matrix, an aqueous carrier, and other additional ingredients described herein.

The shampoo composition may comprise a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

The shampoo composition described herein may comprise a shampoo gel matrix. The shampoo gel matrix comprises (i) from about 0.1% to about 20% of one or more fatty alcohols, alternative from about 0.5% to about 14%, alternatively from about 1% to about 10%, alternatively from about 6% to about 8%, by weight of the shampoo gel matrix; (ii) from about 0.1% to about 10% of one or more shampoo gel matrix surfactants, by weight of the shampoo gel matrix; and (iii) from about 20% to about 95% of an aqueous carrier, alternatively from about 60% to about 85% by weight of the shampoo gel matrix.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable. The shampoo gel matrix surfactants may be a detersive surfactant.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Conditioner Composition

The conditioner compositions described herein comprise (i) from about 0.025% to about 20%, by weight of the conditioner composition, and (ii) a conditioner gel matrix. After applying to the hair a conditioner composition as described herein, the method then comprises rinsing the conditioner composition from the hair. The conditioner composition also comprises a conditioner gel matrix comprising (1) one or more high melting point fatty compounds, (2) a cationic surfactant system, and (3) a second aqueous carrier.

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rinsability from the hair when the consumer rinses off the composition.

The high melting point fatty compound can be included in the conditioner composition at a level of from about 0.1% to about 20%, alternatively from about 1% to about 15%, and alternatively from about 1.5% to about 8% by weight of the composition, in view of providing improved conditioning benefits such as slippery feel during the application to wet hair, softness and moisturized feel on dry hair.

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Leave-on Treatment

The leave-on treatment described herein may comprise from about 0.025% to about 0.25%, alternatively from about 0.05% to about 0.2%, alternatively from about 0.1% to about 0.15% of a compound selected from the group consisting of ethylenediamine-N,N'-disuccinic acid (EDDS), derivatives of ethylenediamine-N,N'-disuccinic acid (EDDS), salts of ethylenediamine-N,N'-disuccinic acid (EDDS), and mixtures thereof, by weight of the leave-on treatment. The leave-on treatment also comprises (1) one or more rheology modifiers and (2) a third aqueous carrier. The leave-on treatment may also include from about 0.025% to about 20%, alternatively from about 0.05% to about 0.5%, alternatively from about 0.1% to about 1% microcapsules, by weight of the leave-on treatment.

The leave-on treatment may include one or more rheology modifiers to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. In an embodiment, the leave-on treatment may comprise from about 0.01% to about 3% of a rheology modifier, alternatively from about 0.1% to about 1% of a rheology modifier, The leave-on treatment may comprise a third aqueous carrier. Accordingly, the formulations of the leave-on treatment can be in the form of pourable liquids (under ambient conditions). Such compositions will therefore typically comprise a third aqueous carrier, which is present at a level of at least 20 wt %, from about 20 wt % to about 95 wt %, or from about 60 wt % to about 85 wt %. The third aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The third aqueous carriers useful in the leave-on treatment include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

pH

The shampoo composition, conditioner composition, and/or leave-on treatment may have a pH in the range from about 2 to about 10, at 25° C. The shampoo composition, conditioner composition, and/or leave-on treatment may have a pH in the range of from about 2 to about 6, alternatively from about 3.5 to about 5, alternatively from about 5.25 to about 7, which may help to solubilize copper and redox metals already deposited on the hair.

Additional Components

The shampoo composition, conditioner composition, and/or leave-on treatment (hair care compositions) described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents (e.g., silicones, hydrocarbon oils, fatty esters), natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

Rinse-Off Formulations

The personal care composition may be a rinse-off formulation that can be applied topically to the skin and/or hair and rinsed from the skin and/or hair within minutes with water. The personal care composition may comprise a primary surfactant. Primary surfactants may comprise from 0.1% to 20%, from about 2% to about 10%, from about 5% to about 10%, or from about 2% to about 5% by weight of the personal care composition. The primary surfactant may comprise one or more anionic surfactants. The personal care compositions may also comprise a secondary surfactant. Secondary surfactants may comprise from 0.1% to 20%, from about 2% to about 10%, or from about 2% to about 5% by weight of the personal care composition. Secondary surfactants may also comprise more than 20% by weight of the personal care composition. The personal care compositions may also contain from about 20% to about 95%, from about 40% to about 90%, from about 60% to about 90%, or from about 70% to about 90% of water, by weight of the personal care composition. The personal care compositions may further comprise a viscosity modifier for modifying the viscosity of the personal care composition. Such concentrations of viscosity modifiers may range, for example, from about 0.1% to about 10%, from about 0.3% to about 5.0%, from about 0.5% to about 10%, or from 0.5% to 3% by weight of the personal care compositions. The personal care compositions may also include other personal care adjunct ingredients that may modify the physical, chemical, cosmetic or aesthetic characteristics of the personal care compositions or serve as "active" components when deposited on the skin. Non-limiting examples of primary surfactants include sodium lauryl sulfate, ammonium lauryl sulfate, sodium laureth sulfate, and ammonium laureth sulfate. Non-limiting examples of secondary surfactants include cocamidopropyl betaine. Non-limiting examples of other ingredients include fragrances and polyols. Non-limiting examples of viscosity modifiers include sodium carbonate, sodium chloride, sodium aluminum sulfate, disodium phosphate, sodium polymetaphosphate, sodium magnesium succinate, sodium sulfate, sodium tripolyphosphate, aluminum sulfate, aluminum chloride.

The rinse-off formulation may be a single-phased or a multi-phased product. Multi-phased is meant that at least two phases herein occupy separate, but distinct physical spaces inside the package in which they are stored, but are in direct contact, with another. The multi-phase product may have a cleansing phase and a benefit phase. The cleansing phase may comprise a surfactant component comprising a surfactant or a mixture of surfactants. Non-limiting examples of these surfactants include anionic, nonionic, cationic, zwitterionic, and amphoteric surfactants, soap, and combinations thereof. The benefit phase may be anhydrous. The multi-phase product may also include a non-lathering, structured aqueous phase that comprises a water structurant and water. The single and/or multi-phase product may also include other ingredients, non-limiting examples of which include humectants, occlusive agents, and fragrances.

Body Spray/Fine Fragrance

The personal care composition may be an aersolized composition (i.e. a composition intended to be aerosolized) like a body spray and/or fine fragrance. The aerosolized compositions described herein may include a volatile solvent or a mixture of volatile solvents. The volatile solvents may comprise greater than or equal to 10%, greater than 30%, greater than 40%, greater than 50%, greater than 60%, or greater than 90%, and less than 99% by weight of the composition. A non-limiting example of a volatile solvent is ethanol. In some examples, the aerosolized composition may comprise from 0.01% to 98%, by weight of the composition, of ethanol. The aerosolized composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof. "Nonvolatile" refers to those materials that are liquid under ambient conditions and which have a measurable vapor pressure at 25° C. These materials typically have a vapor pressure less than about 0.01 mmHg, and an average boiling point typically greater than about 250° C.

The aerosolized composition may also include one or more non-encapsulated fragrances. Generally, the fragrance(s) may be present at a level from about 0.01% to about 40%, from about 0.1% to about 25%, from about 0.25% to about 20%, or from about 0.5% to about 15%, by weight of the composition. Non-limiting examples of fragrances include alcohols, aldehydes, ketones, ethers, Schiff bases, nitriles, and esters. The compositions described herein may include a carrier. Non-limiting examples of carriers include water, silicone oils like silicone D5, and other oils like mineral oil, isopropyl myristate, and perfume oils. If present, the water may comprise from about 0.1% to about 40%, from about 1% to about 30%, or from about 5% to about 20%, by weight, of the composition. In some examples, the aerosolized composition may include a propellant; non-limiting examples of propellants include compressed air, nitrogen, inert gases, carbon dioxide, gaseous hydrocarbons like propane, n-butane, isobutene, cyclopropane, and mixtures thereof. In some examples, the aerosolized composition is aerosolized by the inherent design of the dispenser, such as by the use of a swirl chamber or other internal design. The aerosolized composition may also include other ingredients; non-limiting examples of which include an antiperspirant active (for use in a body spray) or other materials like colorants (for use in a fine-fragrance). In some examples, the aerosolized composition may be substantially free of a material selected from the group consisting of a propellant, a detersive surfactant, and combinations thereof. In some examples, the aerosolized composition includes one or more suspending agents as disclosed herein. In some examples, the aerosolized composition includes from 50% to 99.9%, by weight of the composition, of ethanol; optionally from 0.5% to 50% by weight of the composition of a fragrance; and optionally from 0.01% to about 15% by weight of the composition of a suspending agent.

Antiperspirant/Deodorant

The personal care composition may be an antiperspirant composition/deodorant. The personal care composition may include an antiperspirant active suitable for application to human skin. The concentration of the antiperspirant active in the antiperspirant composition should be sufficient to provide the desired enhanced wetness protection. For example, the active may be present in an amount of from about 0.1%, about 0.5%, about 1%, or about 5%; to about 60%, about 35%, about 25% or about 20%, by weight of the antiperspirant composition. These weight percentages are calculated on an anhydrous metal salt basis exclusive of water and any complexing agents such as glycine, glycine salts, or other complexing agents. Personal care compositions may also include a structurant to help provide the personal care composition with the desired viscosity, rheology, texture and/or product hardness, or to otherwise help suspend any dispersed solids or liquids within the personal care composition. The term "structurant" may include any material known or otherwise effective in providing suspending, gelling, viscosifying, solidifying, or thickening properties to the personal care composition or which otherwise provide structure to the final product form. Non-limiting examples of structurants include, for example, gelling agents, polymeric or nonpolymeric agents, inorganic thickening agents, or viscosifying agents. The concentration and type of the structurant selected for use in the personal care composition may vary depending upon the desired product form, viscosity, and hardness. The personal care compositions may include a surfactant. A surfactant is generally present at a level of about 0.05% to about 5%, by weight of the personal care composition, but may contain, from about 0.5% to about 5.0%; from about 1.0% to about 4%; from about 1.5% to about 3.5%; from about 1.75% to about 2.5%; about 2%, or any combination thereof. Personal care compositions may also include anhydrous liquid carriers. The anhydrous liquid carrier may be present, for example, at concentrations ranging from about 10%, about 15%, about 20%, about 25%; to about 99%, about 70%, about 60%, or about 50%, by weight of the personal care composition. Such concentrations will vary depending upon variables such as product form, desired product hardness, and selection of other ingredients in the personal care composition. The anhydrous carrier may be any anhydrous carrier known for use in personal care compositions or otherwise suitable for topical application to the skin. For example, anhydrous carriers may include, but are not limited to, volatile and nonvolatile fluids. The personal care composition may also include a malodor reducing agent.

Malodor reducing agents include components other than the antiperspirant active within the personal care composition that act to eliminate the effect that body odor has on fragrance display. These agents may combine with the offensive body odor so that they are not detectable including and may suppress the evaporation of malodor from the body, absorb sweat or malodor, mask the malodor, and/or prevent/inhibit microbiological activity from odor causing organisms. The concentration of the malodor reducing agent within the personal care composition should be sufficient to provide such chemical or biological means for reducing or eliminating body odor. Although the concentration will vary depending on the agent used, generally, the malodor reducing agent may be included within the personal care composition from about 0.05%, about 0.5%, or about 1%; to about 15%, about 10%, or about 6%, by weight of the personal care composition. Malodor reducing agents may include, but are not limited to, pantothenic acid and its derivatives, petrolatum, menthyl acetate, uncomplexed cyclodextrins and derivatives thereof, talc, silica and mixtures thereof. Such agents may be used as described in U.S. Pat. No. 6,495,149, issued to Scavone, et al and U.S. patent application 2003/0152539, filed Jan. 25, 2002 in the names of Scavone, et al.

The personal care compositions described herein may include a moisture-triggered fragrance technology delivery system that utilizes cyclic oligosaccharides, starches, starch-derivatives, polysaccharide-based encapsulation systems, and combinations thereof. As used herein, the term "cyclic oligosaccharide" means a cyclic structure comprising six or more saccharide units. The cyclic oligosaccharides may have six, seven, or eight saccharide units or mixtures thereof. It is common in the art to refer to six, seven and eight membered cyclic oligosaccharides as α, β, and γ, respectively. The cyclic oligosaccharides that may be useful include those that are soluble in water, ethanol, or both water and ethanol. The cyclic oligosaccharides useful herein may have a solubility of at least about 0.1 g/100 ml, at 25° C. and 1 atm of pressure in either water, ethanol, or both water and ethanol. The personal care compositions disclosed herein may comprise from about 0.001% to about 40%, from about 0.1% to about 25%, from about 0.3% to about 20%, from about 0.5% to about 10%, or from about 0.75% to about 5%, by weight of the personal care composition, of a cyclic oligosaccharide. The personal care compositions disclosed herein may comprise from 0.001% to 40%, from 1% to 25%, from 0.3% to 20 from 0.5% to 10%, or from 0.75% to 5%, by weight of the personal care composition, of a cyclic oligosaccharide.

The personal care compositions may include one or more fragrances. As used herein, "fragrance" is used to indicate any odoriferous material. Any fragrance that is cosmetically acceptable may be used in the personal care composition. For example, the fragrance may be one that is a liquid at room temperature. Generally, the fragrance(s) may be present at a level from about 0.01% to about 40%, from about 0.1% to about 25%, from about 0.25% to about 20%, or from about 0.5% to about 15%, by weight of the personal care composition. The personal care compositions may also include other materials known for use in antiperspirant, deodorant or other personal care products, including those materials that are known to be suitable for topical application to skin. Non-limiting examples include dyes or colorants, emulsifiers, distributing agents, pharmaceuticals or other topical actives, skin conditioning agents or actives, deodorant agents, antimicrobials, preservatives, surfactants, processing aides such as viscosity modifiers and wash-off aids.

Cosmetic Composition

The personal care composition may take the form of a cosmetic composition that may be applied to mammalian keratinous tissue, including human skin. The cosmetic compositions may take various forms. For example, some non-limiting examples of forms include solutions, suspensions, lotions, creams, gels, toners, sticks, pencils, ointments, pastes, foams, powders, mousses, shaving creams, wipes, strips, patches, electrically-powered patches, wound dressing and adhesive bandages, hydrogels, film-forming products, facial and skin masks, cosmetics (e.g. foundations, eye liners, eye shadows), and the like.

For example, the cosmetic composition may comprise from about 1% to about 95% by weight of water. The cosmetic composition may comprise from about 1% to about 95% by weight of one or more oils. Oils may be used to solubilize, disperse, or carry materials that are not suitable for water or water soluble solvents. Suitable oils include silicones, hydrocarbons, esters, amides, ethers, and mixtures thereof. When the cosmetic composition is in the form of an emulsion, oils are carriers typically associated with the oil phase. The cosmetic composition may be in the form of a water-in-oil emulsion, an oil-in-water emulsion, or a water-in-silicone emulsion such that the cosmetic composition may include water, a silicone, oil, and combinations thereof. The cosmetic compositions may include an emulsifier. An emulsifier is particularly suitable when the cosmetic composition is in the form of an emulsion or if immiscible materials are being combined. The cosmetic composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic, zwitterionic, or cationic. Non-limiting examples of emulsifiers are disclosed in U.S. Pat. No. 3,755,560, U.S. Pat. No. 4,421,769, and McCutcheon's, *Emulsifiers and Detergents*, 2010 Annual Ed., published by M. C. Publishing Co. Structuring agents may be used to increase viscosity, thicken, solidify, or provide solid or crystalline structure to the cosmetic composition. Structuring agents are typically grouped based on solubility, dispersibility, and phase compatibility. Examples of aqueous or water structuring agents include, but are not limited to, polymeric agents, natural or synthetic gums, polysaccharides, and the like. The cosmetic compositions may comprise from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the cosmetic composition, of one or more structuring agents. The cosmetic compositions may optionally contain one or more UV actives. As used herein, "UV active" includes both sunscreen agents and physical sunblocks. Suitable UV actives may be organic or inorganic. Examples of some suitable UV actives are listed in the functional category of "Sunscreen Agents" in the Personal Care Product Council's *International Cosmetic Ingredient Dictionary and Handbook*, Thirteenth Edition, 2010. The cosmetic compositions may be generally prepared by conventional methods such as those known in the art of making cosmetic compositions. Such methods typically involve mixing of ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The cosmetic compositions are preferably prepared such as to optimize stability (physical stability, chemical stability, photostability, etc.) and/or delivery of active materials. The cosmetic composition may be provided in a package sized to store a sufficient amount of the cosmetic composition for a treatment period. The size, shape, and design of the package may vary widely. Certain package examples are described in U.S. Pat. Nos. D570,707; D391,162; D516,436; D535,191; D542,660; D547,193; D547,661; D558,591; D563,221; 2009/0017080; 2007/0205226; and 2007/0040306.

The cosmetic compositions disclosed herein may be applied to one or more skin surfaces and/or one or more mammalian keratinous tissue surfaces as part of a user's daily routine or regimen. Additionally or alternatively, the cosmetic compositions herein may be used on an "as needed" basis. In some examples, an effective amount of the cosmetic composition may be applied to the target portion of the keratinous tissue or skin. In some examples, the cosmetic composition may be provided in a package with written instructions detailing the application regimen.

Hair Colouring/Bleaching Composition

In some examples, the coated microcapsules may be incorporated into personal care composition that is a hair colouring and or bleaching composition. Such hair colouring compositions often are provided as a two part form comprising a first component comprising the oxidising agent and a second component comprising a surfactant system and if present dyes, wherein the first and second component are mixed together prior to the application of the resultant composition onto the hair of the consumer. The coated microcapsules disclosed herein may be used to encapsulate one or more actives in order to provide a 1 part form comprising a first component comprising the oxidising agent and a second component comprising a surfactant system and if present dyes, wherein at least one of the oxidising agent, surfactant system, and dye is encapsulated using the coated microcapsules disclosed herein. In some examples, the oxidizing agent (e.g. inorganic peroxygen material capable of yielding hydrogen peroxide in aqueous solution) is encapsulated in the coated microcapsules and included in the hair colouring/bleaching composition. In other examples, one or more adjunct materials are encapsulated within the coated microcapsules in order to provide a 1 part form.

Non-limiting examples of adjunct materials for hair colouring/bleaching compositions include oxidizing agents such as water-soluble peroxygen oxidizing agents; alkyl glucosides such as a C6 to C16 alkyl glucoside which is comprised within the first or developer composition according to the formula R1-O-(G)x-H wherein R1 is a linear or branched alkyl or alkenyl group comprising from 6 to 16 carbon atoms; associative polymers such as acrylic acid, methacrylic acid or itaconic acid; surfactants such as alkyl ether phosphates having an average of 1 to 20 ethylene oxide units; oxidative dye precursors or developers; non-oxidative pre-formed dyes; carbonate ion sources; additional thickeners and/or rheology modifiers; solvents; radical scavenger; enzymes, additional surfactants; conditioning agents; carriers; antioxidants; stabilizers; chelants; perming actives; perfume; pearling agents; opacifiers; fluorescent dyes; reducing agents (thiolactic acid); hair swelling agents and/or polymers; gel network thickeners; cationic polymers such as polyquaternium 37, polyquaternium 7, polyquaternium 22, polyquaternium 87 and mixtures thereof; alkalizing agents such as those that provide a source of ammonium ions; couplers like phenols; direct dyes like acid yellow 1; conditioning agents like silicones; radical scavengers like monoethanolamine; chelants like EDDS (ethylenediaminedisuccinic acid); solvents like water; and mixtures thereof.

Any oxidizing agent known in the art may be utilized. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can be used if desired. The oxidizing agents may be provided in aqueous solution or as a powder which is dissolved prior to use. In some examples, the oxidizing agent is encapsulated within the coated particles. Non-limiting examples of preferred oxidizing agents are hydrogen peroxide, percarbonate (which may be used to provide a source of both oxidizing agent and carbonate ions), persulphates and combinations thereof.

Suspending Agents

The compositions described herein may include one or more suspending agents to suspend the microcapsules (coated and/or uncoated microcapsules) and other water-insoluble and/or ethanol-insoluble material dispersed in the composition. The concentration of the suspending agent may range from about 0.01% to about 90%, alternatively from about 0.01% to about 15% by weight of the composition, alternatively from about 0.5% to about 15%, alternatively from 0.1% to 15%.

Non-limiting examples of suspending agents include anionic polymers, cationic polymers, and nonionic polymers. Non-limiting examples of said polymers include vinyl polymers such as cross linked acrylic acid polymers with the CTFA name Carbomer, cellulose derivatives and modified cellulose polymers such as methyl cellulose, ethyl cellulose, hydroxyethyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabia gum, tragacanth, galactan, carob gum, guar gum, karaya gum, carrageenan, pectin, agar, quince seed (*Cydonia oblonga* Mill), starch (rice, corn, potato, wheat), algae colloids (algae extract), microbiological polymers such as dextran, succinoglucan, pulleran, starch-based polymers such as carboxymethyl starch, methylhydroxypropyl starch, alginic acid-based polymers such as sodium alginate and alginic acid, propylene glycol esters, acrylate polymers such as sodium polyacrylate, polyethylacrylate, polyacrylamide, and polyethyleneimine, and inorganic water soluble material such as bentonite, aluminum magnesium silicate, laponite, hectonite, and anhydrous silicic acid. Other suspending agents may include, but are not limited to, Konjac, Gellan, and a methyl vinyl ether/maleic anhydride copolymer crosslinked with decadiene (e.g. Stabileze®).

Other non-limiting examples of suspending agents include cross-linked polyacrylate polymers like Carbomers with the trade names Carbopol® 934, Carbopol® 940, Carbopol® 950, Carbopol® 980, Carbopol® 981, Carbopol® Ultrez 10, Carbopol® Ultrez 20, Carbopol® Ultrez 21, Carbopol® Ultrez 30, Carbopol® ETD2020, Carbopol® ETD2050, Pemulen® TR-1, and Pemulen® TR-2, available from. The Lubrizol Corporation; acrylates/steareth-20 methacrylate copolymer with trade name ACRYSOL™ 22 available from Rohm and Hass; acrylates/beheneth-25 methacrylate copolymers, trade names including Aculyn-28 available from DOW, and Volarest™ FL available from Croda; acrylates copolymers with the trade name Aculyn 33 available from DOW; Peg-150/Decyl Alcohol/Smdi Copolymer with the trade name Aculyn 44 available from DOW; nonoxynyl hydroxyethylcellulose with the trade name Amercell™ POLYMER HM-1500 available from Amerchol; methylcellulose with the trade name BENECEL®, hydroxyethyl cellulose with the trade name NATROSOL®; hydroxypropyl cellulose with the trade name KLUCEL®; cetyl hydroxyethyl cellulose with the trade name POLYSURF® 67, supplied by Hercules; ethylene oxide and/or propylene oxide based polymers with the trade names CARBOWAX® PEGs, POLYOX WASRs, and UCON® FLUIDS, all supplied by Amerchol; ammonium acryloyl dimethyltaurate/carboxyethyl-acrylate-crosspolymers like Aristoflex® TAC copolymer, ammonium acryloyl dimethyltaurate/VP copolymers like Aristoflex® AVS copolymer, sodium acryloyl dimethyltaurate/VP crosspolymers like Aristoflex® AVS copolymer, ammonium acryloyl dimethyltaurate/beheneth-25 methacrylate crosspolymers like Aristoflex® BVL or HMB, polyacrylate crosspolymer-11 like Aristoflex Velvet, all available from Clariant Corporation; polyacrylate crosspoylmer-6 with the trade name Sepimax™ Zen, available from Seppic; and cross-linked copolymers of vinyl pyrrolidone and acrylic acid such as UltraThix™ P-100 polymer available from Ashland.

Other non-limiting examples of suspending agents include crystalline suspending agents which can be categorized as acyl derivatives, long chain amine oxides, and mixtures thereof.

Other non-limiting examples of suspending agents include ethylene glycol esters of fatty acids, in some aspects those having from about 16 to about 22 carbon atoms; ethylene glycol stearates, both mono and distearate, in some aspects, the distearate containing less than about 7% of the mono stearate; alkanol amides of fatty acids, having from about 16 to about 22 carbon atoms, or about 16 to 18 carbon atoms, examples of which include stearic monoethanolamide, stearic diethanolamide, stearic monoisopropanolamide and stearic monoethanolamide stearate; long chain acyl derivatives including long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin), a commercial example of which is Thixin® R available from Rheox, Inc. Other non-limiting examples of suspending agents include long chain acyl derivatives, ethylene glycol esters of long chain carboxylic acids, long chain amine oxides, and alkanol amides of long chain carboxylic acids.

Other non-limiting examples of suspending agents include long chain acyl derivatives including N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Non-limiting examples of suitable long chain amine oxides for use as suspending agents include alkyl dimethyl amine oxides (e.g., stearyl dimethyl amine oxide).

Other non-limiting suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Other non-limiting examples of suspending agents include di(hydrogenated tallow) phthalic acid amide, and cross-linked maleic anhydride-methyl vinyl ether copolymer.

Fabric and Home Care Compositions

In some examples, the coated microcapsules are included in a fabric and home care product. As used herein, the term "fabric and home care product" is a cleaning and treatment composition that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which are applicable may be in standard, concentrated or even highly concentrated form even to the extent that such products may in certain aspect be non-aqueous.

The non-limiting list of adjuncts materials illustrated hereinafter are suitable for use in compositions and may be desirably incorporated in certain aspects, for example to assist or enhance cleaning performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the fabric treatment operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents and/or pigments.

As stated, the adjunct ingredients are not necessarily essential. Thus, certain aspects of Applicants' compositions do not contain one or more of the following adjuncts materials: surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems structure elasticizing agents, carriers, hydrotropes, processing aids, solvents and/or pigments.

Packaging

The coated microcapsules may be stored in any container or dispenser known in the art. Non-limiting examples of dispensers are described in EP0775530B 1, EP1633490.

Method of Use

The personal care compositions disclosed herein may be applied to one or more skin surfaces and/or one or more mammalian keratinous tissue surfaces as part of a user's daily routine or regimen. Additionally or alternatively, the compositions herein may be used on an "as needed" basis and used for as intended for the given consumer product. The composition may be applied to any article, such as a textile, or any absorbent article including, but not limited to, feminine hygiene articles, diapers, and adult incontinence articles. For example, the compositions may be used as a body lotion, body spray, feminine spray, adult incontinence spray, baby spray, fine fragrance spray, or other spray. The size, shape, and aesthetic design of the dispensers described herein may vary widely as may the mechanical design of the dispenser.

Test Methods

Test Method for Measuring the Size of the Microcapsules

The dimensions of uncoated and coated microcapsules may be measured using a Malvern Mastersizer Hydro 2000SM particle size analyser. Measurements are performed according to British Standard BS ISO 13099-1:2012 ("Colloidal systems—Methods for zeta-potential determination").

Test Method for Measuring the Size of the Metal Particles

The dimensions of metal particles may be measured by dynamic light scattering. Specifically, a Malvern Nano-ZS Zetasizer and FEI Tecnai TF20 field emission transmission gun electron microscopy (FEGTEM) fitted with HAADF detector and Gatan Orius SC600A CCD camera may be used.

Test Method for Measuring the Thickness of the Polymeric Shell and the Metallic Coating The thickness of the polymeric shell and the metallic coating may be measured using microtoming and FEGTEM. In order to prepare capsule cross-section samples for TEM imaging, 1% of the washed capsules are centrifuged and redispersed in 1 mL of ethanol. The capsule samples are then air dried and mixed with EPO FIX epoxy resin. The sample is left to harden overnight and ~100 nm thick microtome samples are floated onto water and set on TEM grids. FEGTEM is used to generate images of the microtomes and the thickness of the polymeric shell and the metallic coating may be determined using a computer program, such as Image J.

Test Method for Measuring the Adsorption Density of Metal Particles on the Capsule Surface Metal particle surface adsorption densities may be measured directly from TEM images. Adsorption densities can be measured for small sample boxes on the surface of the capsule. The distance from the centre of the sphere is then noted in each case. Each measurement was then corrected for both surface curvature and halved to compensate for the transparent nature of the capsules (TEM imaging shows the metal particles on both sides of the capsule). The size distribution of the capsules is then used to convert the number density obtained from these images to a 2D surface coverage (percent).

Test Method for Measuring the Zeta Potentials of Uncoated Microcapsules, Metal Particles and Coated Microcapsules The zeta potentials of uncoated microcapsules, the metal particles and the coated capsules may be analysed using a Malvern nano-ZS zetasizer. Zeta potentials are measured according to British Standard BS ISO 13099-1:2012 ("Colloidal systems—Methods for zeta-potential determination").

Test Method for Analysing the Chemical Composition of the Coated Microcapsules

The chemical composition of the coated microcapsules may be analysed using an Oxford Instruments INCA 350 energy dispersive X-ray spectroscopy (EDX) with 80 mm X-Max SDD detector, which is installed in FEGTEM; and EDX in FEGTSEM.

Ethanol Stability Test

The Ethanol Stability Test refers to the following test procedure.

A known volume of microcapsules (coated or uncoated microcapsules) are isolated and dispersed in an aqueous solution consisting of 1 part water to 4 parts absolute ethanol. The dispersion is heated to 40° C. After 7 days at 40° C., the microcapsules are isolated from the aqueous solution using centrifugation at 7000 rpm for 1 minute.

The aqueous solution is then subjected to analysis using gas chromatography to determine the content of the liquid core material that has leached from the microcapsules. Samples are assessed using a fused silica column of 3 m in length and 0.25 mm internal diameter, coated with a 0.25 mm film of 100% dimethyl polysiloxane stationary phase. The column temperature is programmed to increase from 50° C. to 300° C. at a rate of 20° C. per minute. A Clarus 580 gas chromatograph is used for the analysis.

Where the loss of liquid core material from coated microcapsules is compared with that from uncoated microcapsules, the uncoated microcapsules may be subjected to the washing steps of the coating procedure, to ensure that there is equivalent liquid core material loss from the coated and uncoated microcapsules in advance of the Ethanol Stability Test.

To confirm the presence of the liquid core material within the coated microcapsules, a known sample of capsules is crushed between two glass slides and washed into a vial with 5 ml ethanol. The capsules are isolated from the aqueous solution using centrifugation at 7000 rpm for 1 minute. The aqueous solution is then subjected to analysis using gas chromatography to determine the content of the liquid core material that has leached from the microcapsules.

EXAMPLES

The following Examples describe and illustrate embodiments within the scope of the present invention. The Examples are given solely for the purpose of illustration and are not to be construed as limitations of the present invention, as many variations thereof are possible without departing from the spirit and scope of the invention. Unless otherwise stated, the test procedures used in these Examples are those specified in the Test Methods section of this specification.

Example 1: Synthesis of Microcapsules Comprising a Polyacrylate Shell and an n-Hexadecane Core The following procedure was used to prepare microcapsules comprising a polyacrylate shell and an n-hexadecane core. Microcapsules were prepared by a coacervation procedure which involved oil-in-water emulsification followed by solvent extraction. Poly(vinyl alcohol) was used as an emulsifier.

2.5 g of poly(methyl methacrylate) (PMMA, 99%, Sigma) was dissolved in 70.5 g of dichloromethane (DCM) (>99%, Acros Organics). 5.0 g of n-hexadecane (99%, Acros Organics) was added to this and mixed until one phase formed. This formed the "core" phase. In a 100 ml volumetric flask, a 2% emulsifier solution was prepared by dissolving a sufficient amount of poly(vinyl alcohol) (PVA, 67 kDa, 8-88 Fluka) in Milli-Q water, to form the "continuous" phase. 7 ml of both the "core" and "continuous" phase was added to a glass vial and emulsified using a homogeniser (IKA T25 Ultra-Turrax) at 15000 rpm for 2 min. The stabilised emulsion was then stirred magnetically at 400 rpm while 86 ml of the "continuous" phase was poured in slowly. The diluted emulsion was then stirred at 400 rpm for 24 hours at room temperature to allow capsule formation to occur. The dispersion was transferred into a separating funnel and the capsules allowed to cream. The aqueous phase of excess PVA was removed, and replaced with Milli-Q water three times. The capsules were redispersed in 50 ml Milli-Q water.

Example 2: Synthesis of Microcapsules Containing a Polyacrylate Shell and a Toluene Core The following procedure was used to prepare microcapsules comprising a polyacrylate shell and a toluene core. Microcapsules were prepared by a coacervation procedure which involved oil-in-water emulsification followed by solvent extraction. Cetyl trimethylammonium bromide was used as an emulsifier.

5 g of poly(ethyl methacrylate) (PEMA, 99%, Sigma) was dissolved in 81 g of dichloromethane (DCM) (>99%, Acros Organics). 14 g of toluene (99%, Acros Organics) was added to this and mixed until one phase formed. This formed the "core" phase. In a 100 ml volumetric flask, a 0.28% emulsifier solution was prepared by dissolving a sufficient amount of cetyl trimethylammonium bromide (CTAB, 98%, Sigma) in Milli-Q water, to form the "continuous" phase. 7 ml of both the "core" and "continuous" phase was added to a glass vial and emulsified using a homogeniser (IKA T25 Ultra-Turrax) at 15000 rpm for 2 min. The stabilised emulsion was then stirred magnetically at 400 rpm while 86 ml of the "continuous" phase was poured in slowly. The diluted emulsion was then stirred at 400 rpm for 24 hours at room temperature to allow capsule formation to occur. The capsules were isolated by washing via centrifugation (Heraeus Megafuge R16) and removing the supernatant three times at 4000 rpm for 5 min. The capsules were redispersed in 25 ml Milli-Q water.

Example 3: Synthesis of Microcapsules Containing a Polyacrylate Shell and a Hexyl Salicylate Core The following procedure was used to prepare microcapsules comprising a polyacrylate shell and a hexyl salicylate core. Microcapsules were prepared by a coacervation procedure which involved oil-in-water emulsification followed by solvent extraction. Poly(vinyl alcohol) was used as an emulsifier.

10 g of poly(methyl methacrylate) (PMMA, 99%, Sigma) was dissolved in 60 g of dichloromethane (DCM) (>99%, Acros Organics). 30 g of hexyl salicylate (Procter and Gamble) was added to this and mixed until one phase formed. This formed the "core" phase. In a 100 ml volumetric flask, a 0.28% emulsifier solution was prepared by dissolving a sufficient amount of cetyl trimethylammonium bromide (CTAB, 98%, Sigma) in Milli-Q water, to form the "continuous" phase. 7 ml of both the "core" and "continuous" phase was added to a glass vial and emulsified using a homogeniser (IKA T25 Ultra-Turrax) at 15000 rpm for 2 min. The stabilised emulsion was then stirred magnetically at 400 rpm while 86 ml of the "continuous" phase was poured in slowly. The diluted emulsion was then stirred at 400 rpm for 24 hours at room temperature to allow capsule formation to occur. The capsules were isolated by washing via centrifugation (Heraeus Megafuge R16) and removing the supernatant three times at 4000 rpm for 5 min. The capsules were redispersed in 50 ml Milli-Q water.

Example 4: Preparation of Charge-Stabilised Gold Nanoparticles

The following procedure was used to prepare borohydride-stabilised gold nanoparticles.

0.34 g $HAuCl_4$ was dissolved in Milli-Q water in a 25 ml volumetric flask. 0.036 g HCl was dissolved in Milli-Q water in a 25 ml volumetric flask. The $HAuCl_4$ and HCl solutions were combined in a separate flask. 1.25 ml of this was added dropwise to 47.25 ml Milli-Q water and stirred vigorously. A borohydride solution was prepared by adding 0.095 g $NaBH_4$ dissolved in 25 ml Milli-Q water, to 0.1 g NaOH dissolved in 25 ml Milli-Q water. 1.5 ml of this was added all at once, and the solution was stirred for 1 minute. The solution changed colour from pale yellow to dark ruby red indicating formation of Au nanoparticles.

Example 5: Adsorption of Charge-Stabilised Gold Nanoparticles onto Microcapsules The following procedure was used to adsorb the charge-stabilised gold nanoparticles of Example 4 onto the surface of the microcapsules of Examples 2 and 3.

6 ml of the Au nanoparticles were added to a beaker and stirred vigorously. 0.5 ml microcapsules were added dropwise, and stirred vigorously for a further 10 minutes. The microcapsules were collected by centrifuging (Heraeus Megafuge R16) and removing the supernatant four times at 4000 rpm for 10 min, to remove excess nanoparticles, and were then redispersed in water (2 ml).

Example 6: Preparation of Sterically-Stabilised Platinum Nanoparticles

The following procedure was used to prepare poly(vinyl pyrrolidone)-stabilised platinum nanoparticles.

0.5 g of poly(vinyl pyrrolidone) (PVP, 40 kDa, Fluka) was dissolved in 250 ml Milli-Q water. 31.25 ml of this was added to a 1 L volumetric flask and filled to 1 L with Milli-Q water to give a 0.00625 wt % solution of PVP. 100 ml of this PVP solution was placed in a 250 ml conical flask and 0.23 g of $H_2PtCl_6.6H_2O$ was added and stirred to dissolve. A 0.5 mM solution of $NaBH_4$ was made by dissolving 0.189 g $NaBH_4$ in 10 ml Milli-Q water. 0.4 ml of this was added to the platinum salt-PVP solution with vigorous stirring for 2 minutes. The solution immediately turned dark brown and was left to stand overnight to form Pt-PVP nanoparticles.

Example 7: Adsorption of Sterically-Stabilised Platinum Nanoparticles onto Microcapsules The following procedure was used to adsorb the PVP-stabilised platinum nanoparticles of Example 6 onto the surface of the microcapsules of Examples 1-3.

2 ml of capsules were added to 5 ml of PVP-stabilised platinum nanoparticles in a 40 ml glass vial, and mixed on a carousel for 10 min. The capsules were then washed by centrifugation at 4000 rpm for 5 minutes, three times. The capsules were redispersed in 30 ml Milli-Q water.

Example 8: Adsorption of Platinum Nanoparticles onto Microcapsules Via Reduction In Situ The following procedure was used to adsorb platinum nanoparticles via reduction in situ onto the surface of the microcapsules of Examples 1-3.

In a 100 ml volumetric flask, 0.023 g of $H_2PtCl_6.6H_2O$ was dissolved in Milli-Q water up to 100 ml. 50 ml of this was placed in a conical flask and 1.25 ml capsules was added and stirred vigorously for 30 min. 0.075 g of $NaBH_4$ (Aldrich) was dissolved to 100 ml with Milli-Q water. 50 ml of this was added drop-wise. Vigorous stirring was continued for 30 min. The capsules were then washed by separation for 72 h, allowing the excess Pt to sediment and capsules to cream. The excess Pt and water was removed using a 50 ml pipette and the capsules were redispersed in 7.5 ml Milli-Q water.

Example 9: Formation of Silver Film by Electroless Plating

The following procedure was used to form a continuous silver film on the microcapsules of Example 5 by electroless plating.

2 ml of microcapsules were added to a beaker containing 47.5 ml Milli-Q water. 0.5 ml of 0.1M $AgNO_3$ (99%, Sigma) was added and stirred vigorously. Then 50 µl of formaldehyde (35% in $H_2O$, Sigma) was added, followed by 26 µl of ammonia (25% in $H_2O$, Sigma) to control the pH to ~10, giving a silver-grey dispersion. The dispersion was then stirred for 10 min after which it was centrifuged at 4000 rpm for 10 min, 3 times, for washing, replacing the supernatant each time with Milli-Q water.

Example 10: Formation of Gold Film by Electroless Plating

The following procedure was used to form a continuous gold film on the surface of the microcapsules of Examples 7 and 8 by electroless plating.

1.58 g of $HAuCl_4$ (99.9%, Sigma) was dissolved to 100 ml with Milli-Q water. 0.58 g of hydrogen peroxide (35% in water, Aldrich) was dissolved to 100 ml with Milli-Q water. 0.2 g of poly(vinyl pyrrolidone) was dissolved to 100 ml with Milli-Q water. 1 ml of each of the above solutions was added to a 40 ml glass vial to form the plating solution. 7.5 ml of the microcapsules was added dropwise to the plating solution and stirred vigorously for 5 min. The capsules were washed by centrifugation at 4000 rpm for 5 minutes, three times.

Example 11: Characterisation of Microcapsules Comprising a Pt/Au Metallic Coating Coated microcapsules comprising a PMMA shell, a hexadecane core and a metallic coating comprising a gold film disposed on a layer of platinum nanoparticles were prepared following the procedures described in Examples 1, 8 and 10. The coated microcapsules were then characterised using SEM and TEM.

Figure 2A:
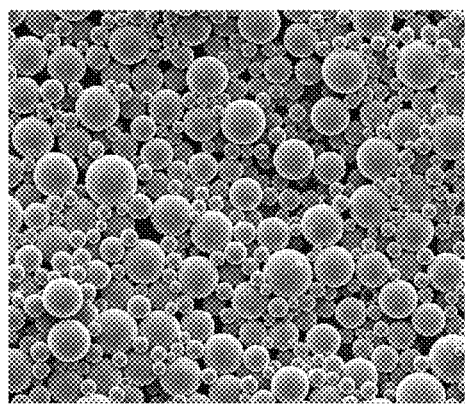
FIGS. 2A, 2B, and 2C provide SEM and TEM images obtained at various stages of preparation of a coated microcapsule comprising a poly(methyl methacrylate) (PMMA) shell, a hexadecane core and a metallic coating comprising a continuous gold film formed on a layer of platinum nanoparticles. Shown are.
Figure 2B:
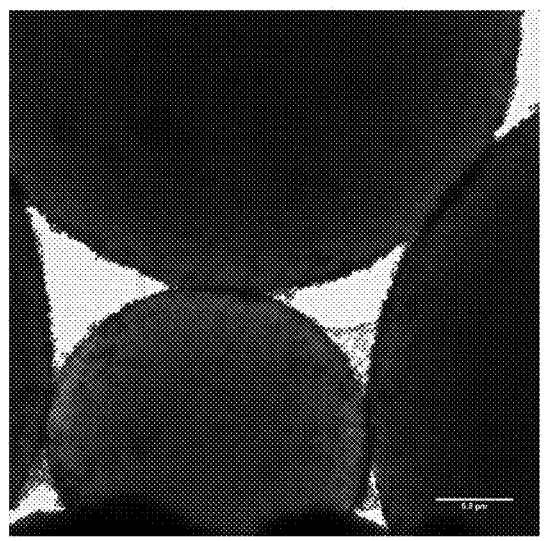
Figure 2C:
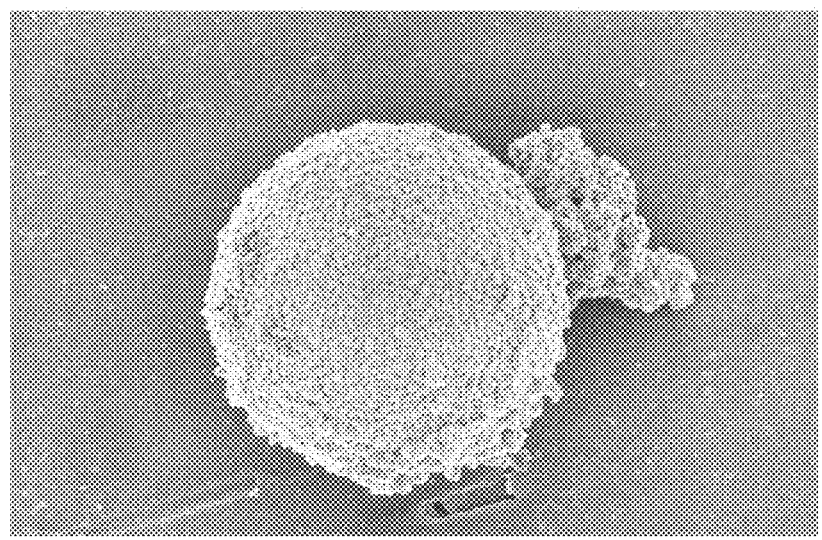

FIG. 2A is an SEM image of the uncoated PMMA microcapsules. FIG. 2B is a TEM image showing the platinum nanoparticles adsorbed on the outer surface of the PMMA microcapsules. FIG. 2C is an SEM image showing the continuous gold film. The maximum thickness of the metallic coating was less than 200 nm in this example, but it will be appreciated that the thickness of the coating may be varied.

Example 12: Characterisation of Microcapsules Comprising an Au/Ag Metallic Coating Coated microcapsules comprising a PEMA shell, a toluene core and a metallic coating comprising a silver film disposed on a layer of borohydride-stabilised gold nanoparticles were prepared following the procedures described in Examples 2, 4, 5 and 9. The coated microcapsules were then characterised using optical microscopy, SEM, TEM and EDX.

Figure 3D:
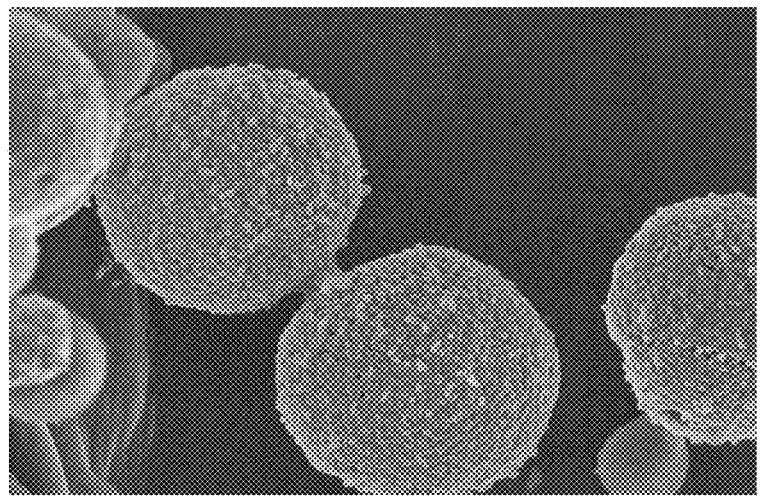
Figure 3E:
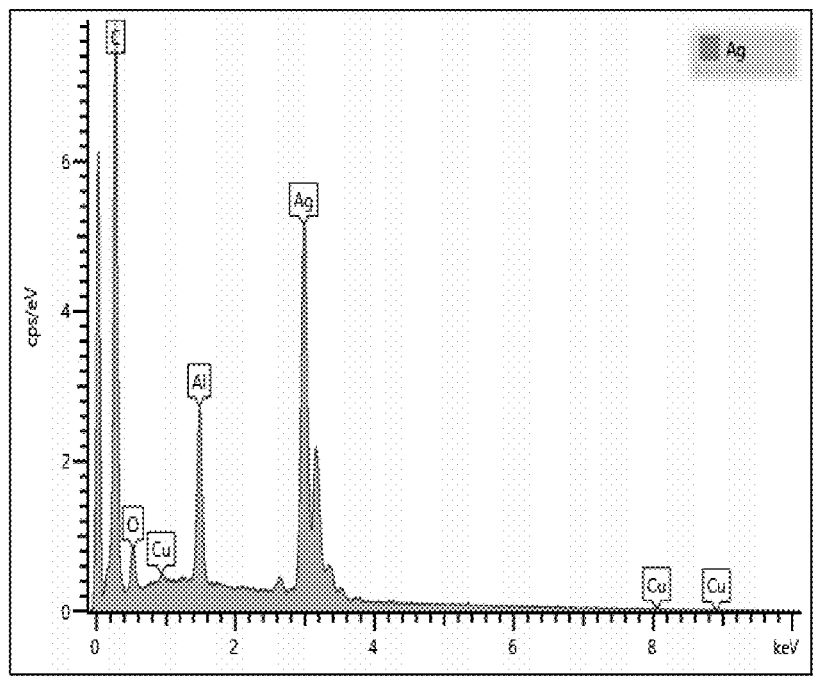
Figures 4A, 4B, 4C, 4D, 4E:
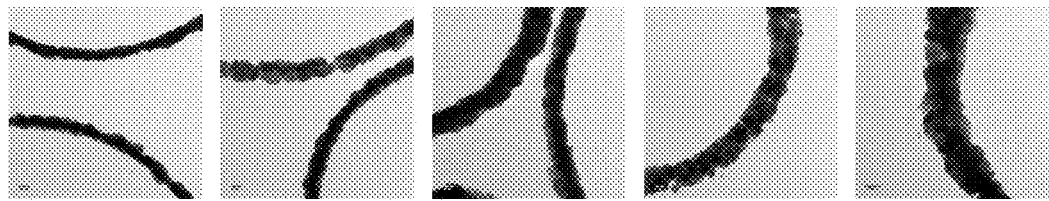
FIG. 4 is a series of TEM images shown in 4a, 4b, 4c, 4d, 4e showing metallic films of varying thicknesses.
Figure 5:
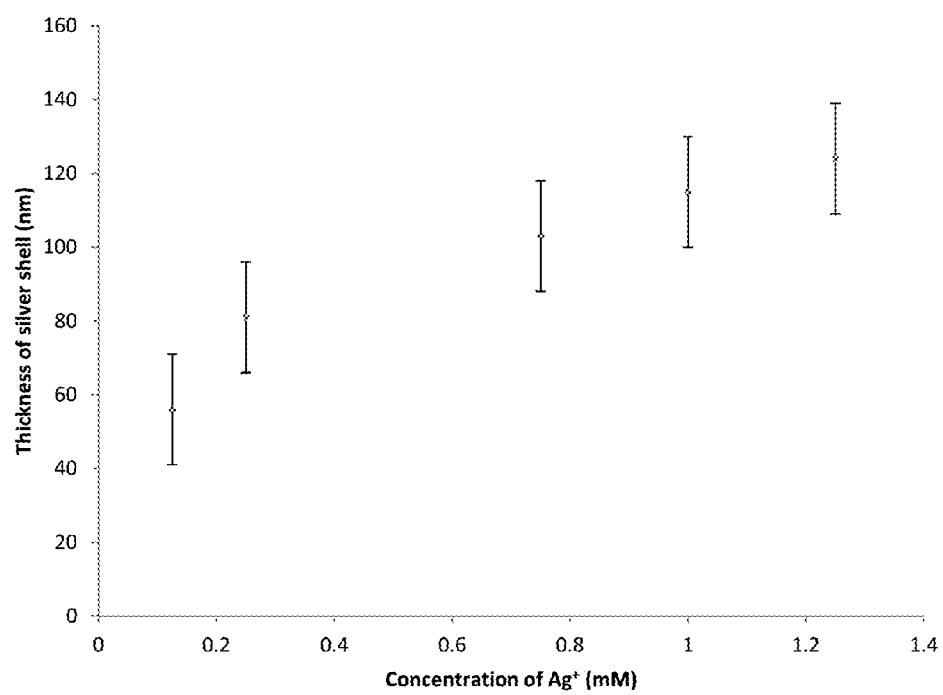
FIG. 5 is a graph which illustrates that the thickness of the metallic coating may be modified by varying the concentration of silver ions in the electroless plating solution.

FIG. 3A is an optical micrograph showing the uncoated PEMA microcapsules. FIGS. 3B and 3C are a TEM image showing the borohydride-stabilised gold nanoparticles adsorbed on the surface of the microcapsules. FIG. 3D is an SEM image showing the continuous silver film. FIG. 3E is an EDX graph of the silver film. The maximum thickness of the metallic coating was 140 nm in this example, but it will be appreciated that the thickness of the coating may be varied. Reference is made in this regard to FIGS. 4A, 4B, 4C and 4D and 5, which illustrate that the thickness of the metallic coating may be modified by, for example, varying the concentration of silver ions in the electroless plating solution.

Example 13: Characterisation of Microcapsules Comprising a Pt/Au Metallic Coating Coated microcapsules comprising a PMMA shell, a hexyl salicylate core and a metallic coating comprising a gold film disposed on a layer of PVP-stabilised platinum nanoparticles were prepared following the procedures described in Examples 3, 6, 7 and 10. The coated microcapsules were then characterised using optical microscopy, SEM and TEM.

Figure 6A:
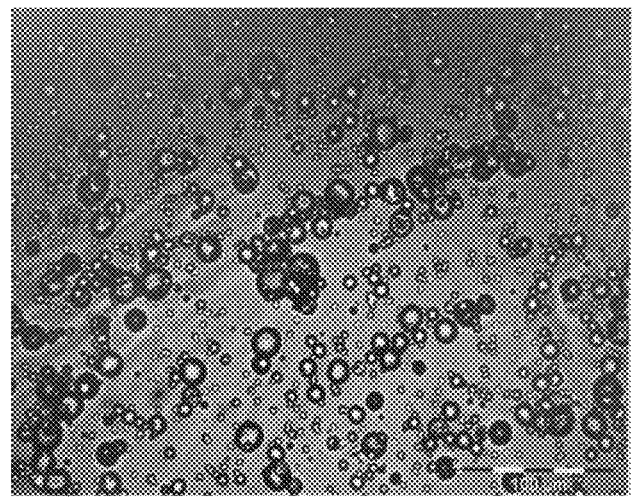
FIGS. 6A, 6B, and 6C provide optical, SEM and TEM images obtained at various stages of preparation of a coated microcapsule, the microcapsule comprising a PMMA shell, a hexyl salicylate core and a metallic coating comprising a layer of PVP-stabilised platinum nanoparticles and a continuous gold film disposed thereon. Shown are.
Figure 6B:
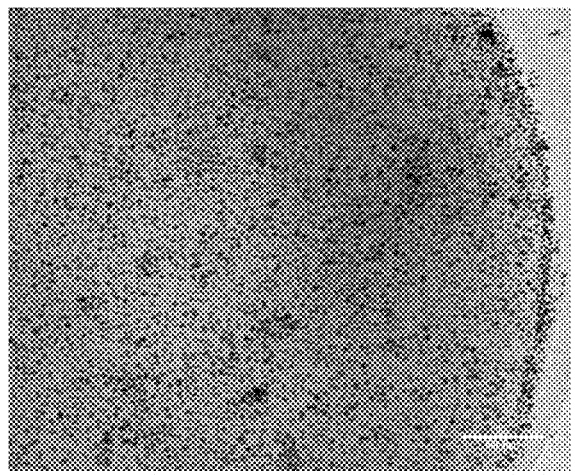
Figure 6C:
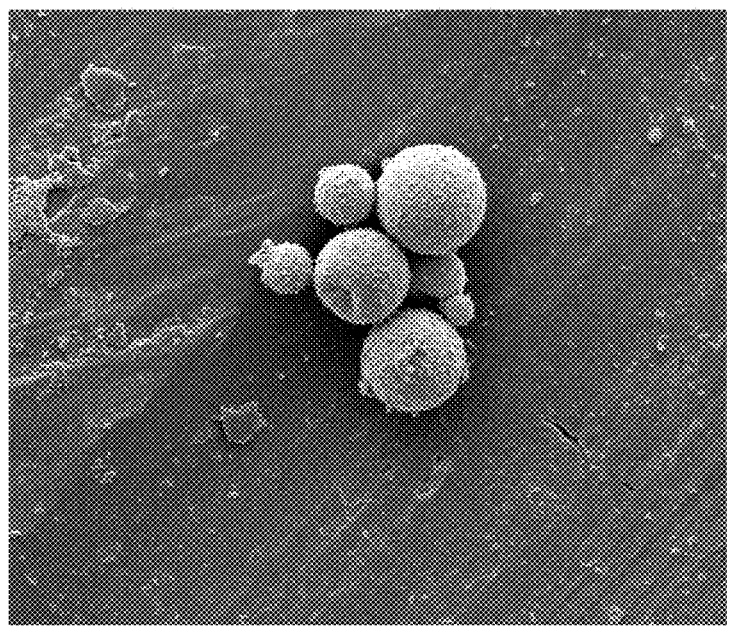

FIG. 6A is an optical micrograph showing the uncoated PMMA microcapsules. FIG. 6B is a TEM image showing the PVP-stabilised platinum nanoparticles adsorbed on the surface of the microcapsules. FIG. 6C is an SEM image showing the gold film on the microcapsules. The maximum

Example 14: Performance of Coated Microcapsules Under the Ethanol Stability Test Coated microcapsules comprising a PMMA shell, a hexadecane core and a metallic coating comprising a layer of platinum nanoparticles and a continuous gold film disposed thereon was prepared following the procedures described in Examples 1, 8 and 10. The coated microcapsules were then tested for their ability to retain the liquid core material using the Ethanol Stability Test described herein, and their performance was compared with that of uncoated PMMA microcapsules.

Figure 7A:
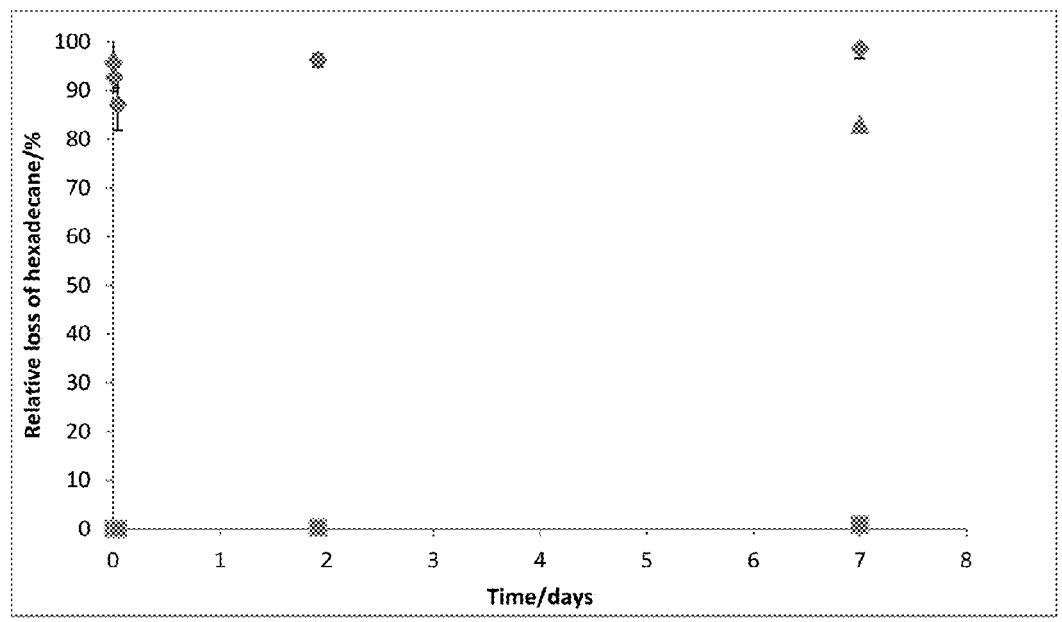
FIG. 7A is a graph showing the performance of coated PMMA microcapsules (data points indicated as squares) and uncoated PMMA microcapsules (data points indicated as diamonds) under the Ethanol Stability Test described herein. Also provided is a data point obtained after fracturing the coated PMMA microcapsules at the end of the experiment (see the data point indicated as a triangle).
Figure 7B:
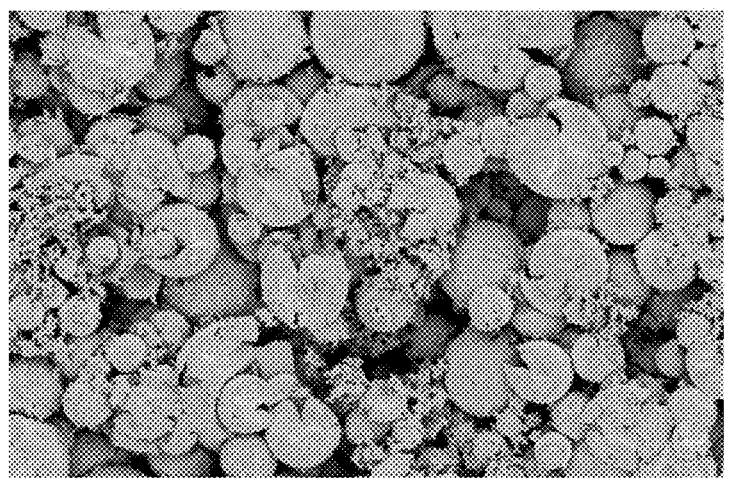
FIG. 7B is an SEM image showing the fractured microcapsules.

FIG. 7A is a graph showing the performance of the coated PMMA and uncoated PMMA microcapsules under the Ethanol Stability Test (see the data points indicated as squares and diamonds respectively). Also shown in FIG. 7A is a data point obtained following fracture of the coated PMMA microcapsules at the end of the experiment (see the data point indicated as a triangle), confirming that the liquid core material had been encapsulated. The fractured microcapsules are depicted in FIG. 7B. It can be seen from these data that the coated microcapsules exhibited negligible leakage of the liquid core material. In contrast, more than 50% of the liquid core material had leaked from the uncoated microcapsules after one day.

Example 15: Synthesis of Microcapsules Comprising a Melamine Formaldehyde Shell and a Soybean Oil Core The following procedure was used to prepare microcapsules comprising a melamine formaldehyde shell and a liquid core comprising soybean oil. Microcapsules were prepared by an in situ polymerisation process in which a butyl acrylate-acrylic acid copolymer and poly(vinyl alcohol) were used as emulsifiers.

0.9 g of butyl acrylate-acrylic acid copolymer (Colloid C351, 2% solids, Kemira), and 0.9 g of poly(acrylic acid) (PAA, 100 kDa, 35% in water Sigma) were dissolved in 20 g of Milli-Q water. An amount of sodium hydroxide was added to this solution to adjust the pH to 3.5.

0.65 g of partially methylated methylol melamine resin (Cymel 385, 80% solids, Cytec) and 20 g of hexyl salicylate were added whilst mixing at 1000 rpm for 60 minutes. In a separate container, 1.0 g of butyl acrylate-acrylic acid copolymer was mixed with 2.5 g of partially methylated methylol melamine resin in 12 g of Milli-Q water. An amount of sodium hydroxide was added to this to adjust the pH to 4.6. This was added to the main mix along with 0.4 g of sodium sulfate (Sigma). The mixture was heated to 75° C. and the temperature maintained for 6 h with continuous stirring at 400 rpm.

Example 16: Synthesis of Microcapsules Comprising a Polyacrylate Shell and a Core Comprising Soybean Oil and Isopropyl Myristate The following procedure was used to prepare microcapsules comprising a polyacrylate shell and a liquid core comprising soybean oil and isopropyl myristate. Microcapsules were prepared by an interfacial polymerisation procedure in which poly(vinyl pyrrolidone) was used as an emulsifier.

15.0 g of hexyl acetate was mixed with 3.75 g of isopropyl myristate at 400 rpm until a homogenous solution was obtained. 15.0 g of the solution was placed in a three-neck round-bottom flask and mixed at 1000 rpm using a magnetic stirrer.

The temperature was increased to 35° C., then 0.06 g of 2,2-azobis-2,4-dimethyl-pentanenitrile (Vazo-52, Du Pont) and 0.02 g of 2,2-azobis(2-methylbutyronitrile) (Vazo-67, Du Pont) were added to the reactor, with a nitrogen blanket applied at 100 cm$^3$.min$^{-1}$ The temperature was increased to 75° C. and held for 45 minutes before being cooled to 60° C. slowly.

The remaining oil-myristate solution was mixed with 0.05 g of t-butylaminoethyl methacrylate (Sigma), 0.04 g of 2-carboxyethyl acrylate (Sigma), and 1.95 g of hexafunctional aromatic urethane-acrylate oligomer (CN9161, Sartomer) at 400 rpm, until homogeneous. The mixture was degassed using nitrogen. At 60° C., this mixture was added to the reaction vessel and maintained at 1000 rpm at 60° C. for 10 minutes, before stirring was stopped.

2.0 g of poly(diallyl dimethyl ammonium chloride) (pDADMAC, 32% active, Sigma) was dissolved in 23.6 ml Milli-Q water. 0.11 g of 20% sodium hydroxide solution, then 0.12 g of 4,4-azobis(cyanovaleric acid) (Vazo-68 WSP, Du Pont) was added and stirred at 400 rpm until it dissolved.

The oil-monomer solution was added t to the pDADMAC solution. Mixing was then restarted at 1000 rpm for 60 minutes. The mixture was then heated slowly to 75° C. and held at this temperature for 12 h with stirring at 400 rpm.

Example 17: Preparation of Charge-Stabilised Gold Nanoparticles

The following procedure was used to prepare borohydride-stabilised gold nanoparticles.

0.34 g HAuCl$_4$ was dissolved in Milli-Q water in a 25 ml volumetric flask. 0.036 g HCl was dissolved in Milli-Q water in a 25 ml volumetric flask. The HAuCl$_4$ and HCl solutions were combined in a separate flask. 1.25 ml of this was added dropwise to 47.25 ml Milli-Q water and stirred vigorously. A borohydride solution was prepared by adding 0.095 g NaBH$_4$ dissolved in 25 ml Milli-Q water, to 0.1 g NaOH dissolved in 25 ml Milli-Q water. 1.5 ml of this was added all at once, and the solution was stirred for 1 minute. The solution changed colour from pale yellow to dark ruby red indicating formation of Au nanoparticles.

Example 18: Adsorption of Charge-Stabilised Gold Nanoparticles onto Microcapsules The following procedure was used to adsorb the charge-stabilised gold nanoparticles of Example 17 onto the surface of the microcapsules of Examples 15 and 16.

5 ml of the Au nanoparticles were added to a beaker and stirred vigorously. 2 ml microcapsules were added dropwise, and stirred vigorously for a further 10 minutes. The microcapsules were collected by centrifuging (Heraeus Megafuge R16) and removing the supernatant four times at 4000 rpm for 10 min, to remove excess nanoparticles, and were then redispersed in water (20 ml).

Example 19: Formation of Silver Film by Electroless Plating

The following procedure was used to form a continuous silver film on the microcapsules of Example 18 by electroless plating.

5 ml of microcapsules were added to a beaker containing 30 ml Milli-Q water. 0.5 ml of 0.1M AgNO$_3$ (99%, Sigma) was added and stirred vigorously. Then 50 µl of formaldehyde (35% in H$_2$O, Sigma) was added, followed by 26 µl of ammonia (25% in H$_2$O, Sigma) to control the pH to ~10, giving a silver-grey dispersion. The dispersion was then stirred for 10 min after which it was centrifuged at 4000 rpm for 10 min, 3 times, for washing, replacing the supernatant each time with Milli-Q water.

Example 20: Characterisation of Microcapsules Comprising a Melamine Formaldehyde Shell and an Au/Ag Metallic Coating Coated microcapsules comprising a melamine formaldehyde shell, a soybean oil core and a metallic coating comprising a silver film disposed on a layer of borohydride-stabilised gold nanoparticles were prepared following the procedures described in Examples 15 and 17-19. The coated microcapsules were then characterised using optical microscopy, SEM, TEM and EDX.

The coated microcapsules were then tested for their ability to retain the liquid core material using the Ethanol Stability Test described herein, and their performance was compared with that of uncoated melamine formaldehyde microcapsules. Whereas the coated microcapsules exhibited negligible leakage of the liquid core material, more than 50% of the liquid core material had leaked from the uncoated microcapsules after one day.

Example 21: Characterisation of Microcapsules Comprising a Polyacrylate Shell and an Au/Ag Metallic Coating Coated microcapsules comprising a polyacrylate shell, a core containing hexyl acetate and isopropyl myristate, and a metallic coating comprising a silver film disposed on a layer of borohydride-stabilised gold nanoparticles were prepared following the procedures described in Examples 16-19. The coated microcapsules were then characterised using optical microscopy, SEM, TEM and EDX.

The coated microcapsules were then tested for their ability to retain the liquid core material using the Ethanol Stability Test described herein, and their performance was compared with that of uncoated polyacrylate microcapsules. Whereas the coated microcapsules exhibited negligible leakage of the liquid core material, more than 50% of the liquid core material had leaked from the uncoated microcapsules after one day.

Example 22: Fine Fragrance Composition

| Example 22 | (% w/w) |
|---|---|
| Ethanol (96%) | 74.88 |
| Fragrance | 11 |
| Coated Microcapsules of Example 16 | 3 |
| Water | 10.82 |
| Diethylamino Hydroxybenzol Hexyl Benzoate | 0.195 |
| Ethylhexyl Methoxycinnamate | 0.105 |

Example 23A-23D: Fine Fragrance Composition

|  | Ex. 23A (% w/w) | Ex. 23B (% w/w) | Ex. 23C (% w/w) | Ex. 23D (% w/w) |
|---|---|---|---|---|
| Ethanol (96%) | 74.88 | 74.88 | 74.88 | 74.88 |
| Fragrance (non-encapsulated) | 11 | 11 | 11 | 11 |
| Coated Microcapsules of Ex. 19 (Derived from Ex. 15 liquid core comprising) | 3 | 0 | 0 | 0 |
| Coated Microcapsules of Ex. 19 (Derived from Ex. 16) | 0 | 3 | 0 | 0 |
| Coated Microcapsules of Ex. 19 (Derived from Ex. 15, wherein the liquid material further includes ionone beta) | 0 | 0 | 3 | 0 |
| Microcapsules of Ex. 19 (Derived from Ex. 16, wherein the liquid material further includes ionone beta) | 0 | 0 | 0 | 3 |
| Water | 10.82 | 10.82 | 10.82 | 10.82 |
| Diethylamino Hydroxybenzol Hexyl Benzoate | 0.195 | 0.195 | 0.195 | 0.195 |
| Ethylhexyl Methoxycinnamate | 0.105 | 0.105 | 0.105 | 0.105 |

Example 24: Hair Colouring/Bleaching Composition

| Ingredient | Example 24 |
|---|---|
| Water | 70.965% |
| Disodium EDTA | 0.045% |
| Aculyn 22 | 0.75% |
| Aculyn 33 | 2.5% |
| Simethicone | 0.025% |
| Coated Microcapsules (Core Material Includes Hydrogen peroxide 35% by weight of the coated microcapsule) | 12.855% |
| Decyl glucoside | 1% |
| Disodium phosphate | 0.04% |
| Sodium lauryl sulphate | 0.05% |
| Phosphoric acid | 0.08% |
| Propylene glycol | 0.05% |

-continued

| Ingredient | Example 24 |
|---|---|
| Erythorbic acid | 0.2% |
| Sodium sulphate | 0.8% |
| Ammonium hydroxide (25% soln.) | 4.35% |
| Crodafos CES ® | 2.5% |
| Cetearyl alcohol | 0.375% |
| Steareth-200 | 0.125% |
| Xanthan gum | 0.04% |
| Propylene glycol | 0.25% |
| Sodium hydroxide | 0.11525% |

Example 25

A gold coating is placed on the surface of a melamine formaldehyde walled perfume microcapsule (MF-PMC). There are generally two steps. The first step is the addition of Pt to coat the surface of the MF-PMC. The second step is the addition of Au on the Pt coated MF-PMC surface. Lastly, scanning electron microscopy (SEM) images are provided.

The MF-PMC is generally made according to the U.S. Pat. No. 8,940,395 and available from Appleton Papers Inc. (USA). The MF-PMC is supplied as spray dried powder. Fracture strength data of these MF-PMC is 1-3 MPa as measured before being spray dried into a powder. It is not known whether spray drying impacts fracture strength. The target particle size for the MF-PMC is 18 microns (volume weighted median particle size) i.e., the largest number of MF-PMC (by volume) are at a particle size of 18 microns.

The first step is conducted either as an in situ reduction approach or as a sterically stabilized Pt nanoparticle adsorption approach. The in situ approach is described. Addition of Pt to the surface of the MF-PMC is described. 500 mg MF-PMC particles is dispersed in 20 g water and sonicated for 30 minutes to suspend particles and break up aggregates. 0.23 g $H_2PtCl_6$ is dissolved in 100 ml water. 0.076 g $NaBH_4$ is dissolved in 100 ml water. 2 mL of MF-PMC dispersion is added to 25 mL of $H_2PtCl_6$ solution and stirred for 30 mins 25 mL of $NaBH_4$ is then added and stirred using a magnetic stirrer for a further 90 mins. The resultant suspension is centrifuged (4000 rpm for 10 mins) and washed with 25 mL distilled water. The process is repeated 2 more times.

The adsorption approach is described. Firstly, a Pt nanoparticle suspension is made. 0.23 g $H_2PtCl_6$ is dissolved in 100 mL poly(vinyl pyrrolidone) ("PVP") (1.56 uM) 0.4 mL $NaBH_4$ (0.2 M) is added and the suspension stirred at high speed for 2 minutes. The nanoparticle suspension is then left to stand overnight. Secondly, the nanoparticle suspension is added to the MF-PMC. 500 mg of the MF-PMC particles is dispersed in 20 g water and sonicated for 30 mins to suspend particles and break up aggregates. 5 mL of the Pt nanoparticle suspension is diluted with another 5 mL water. 1 mL of the MF-PMC particle suspension is added to the diluted Pt nanoparticle suspension. The combined suspensions are allowed to stir for 60 minutes on a carousel. Thereafter, the resultant suspension is centrifuged (4000 rotations per minute (rpm) for 10 minutes) and washed with 25 mL distilled water. The process is repeated 2 more times.

The second step of coating Au on Pt coated MF-PMC surface is described. This second step is the same regardless of the approach used in the first step. 1 ml of $HAuCl_4$ (40 mM), 1 ml $H_2O_2$ (60 mM) and 3 mL PVP (0.2 wt %) are added to a glass vial. 1 mL of nanoparticle coated MF-PMC are added to this and stirred on a carousel for 10 minutes. The resultant suspension is centrifuged (4000 rpm for 5 minutes) and washed with 25 mL distilled water. The process is repeated 2 more times.

Figure 8:
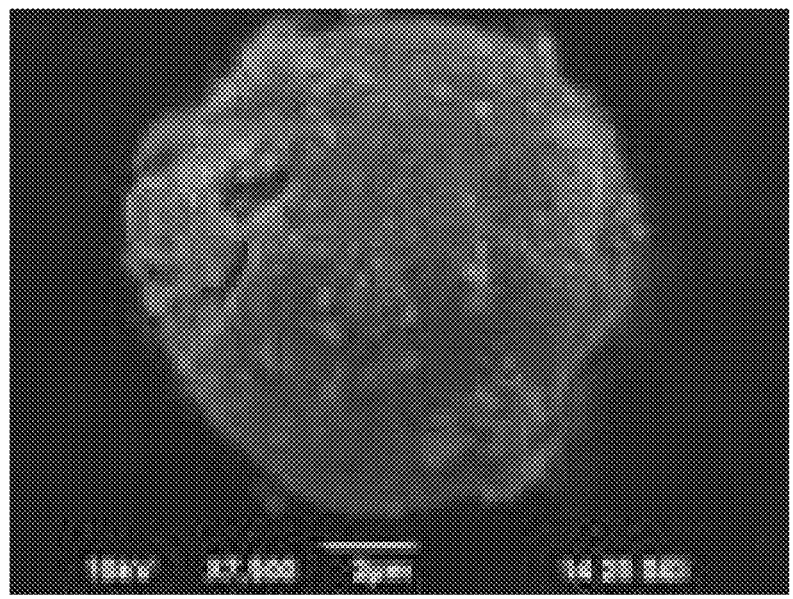
FIG. 8 is an SEM image of a melamine formaldehyde walled perfume microcapsule having a full coating of gold.
Figure 9:
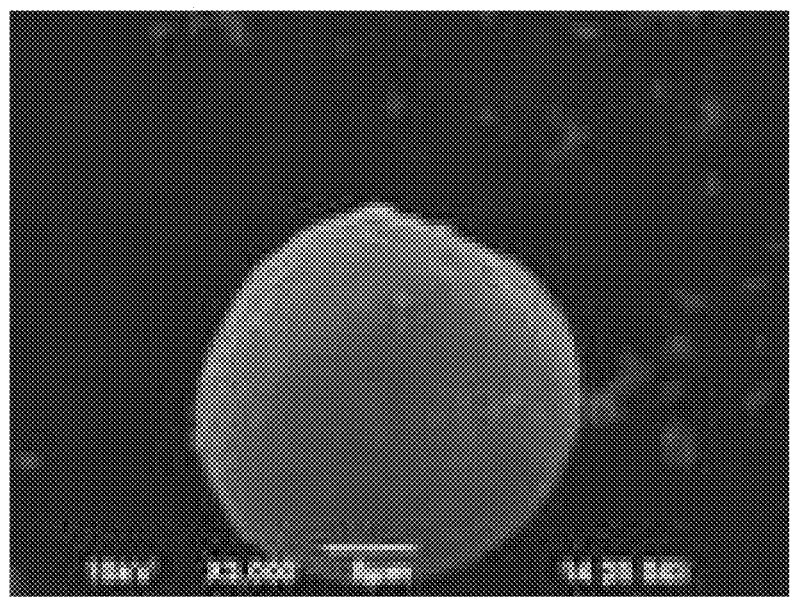
FIG. 9 is an SEM image of a melamine formaldehyde walled perfume microcapsule having a gold coating.

As can be seen in the SEM images of FIGS. 8 and 9, a gold coating is achieved for the MF-PMC. FIG. 8 is the in situ reduction approach ostensibly achieving a full coating of gold. FIG. 9 is the PVP stabilized approach where the surface of the MF-PMC achieves a gold coating.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product comprising a composition, said composition comprising:
   an adjunct material; and
   a plurality of coated microcapsules, said coated microcapsule comprising
   i) a microcapsule comprising a polymeric shell and a liquid core material encapsulated therein; and
   ii) a metallic coating surrounding said microcapsule;
   wherein the metallic coating comprises sterically stabilized nanoparticles of a first metal having a particle size of less than 100 nm adsorbed on said polymeric shell to form a discontinuous layer and a continuous film of a second metal overlaid onto the discontinuous layer by electroless plating catalyzed by the nanoparticles of the first metal;

wherein the sterically stabilized nanoparticles of a first metal are first neutral metal nanoparticles on the surfaces of which are adsorbed and coated a polymeric stabilizer;

wherein the metallic coating has a maximum thickness of 1000 nm wherein the continuous film of a second metal is substantially uniform; and the coated microcapsules retain more than 50% by weight of the liquid core material as shown by an ethanol stability leakage test comprising combining the coated microcapsules in an aqueous solution of one part water and four parts ethanol to form a test mixture, exposing the text mixture to heat at 40° C. for seven days, thereafter separating the text mixture into the coated microcapsules and an aqueous test solution, and analyzing the aqueous test solution to determine the amount of liquid core material that has leached from the coated microcapsules.

2. The consumer product of claim 1, wherein the liquid core material is selected from the group consisting of perfumes; brighteners; insect repellants; silicones; waxes; flavors; vitamins; fabric softening agents; depilatories; skin care agents; enzymes; probiotics; dye polymer conjugate; dye clay conjugate; perfume delivery system; sensates; attractants; anti-bacterial agents; dyes; pigments; bleaches; flavorants; sweeteners; waxes; pharmaceuticals; fertilizers; herbicides and mixtures thereof.

3. The consumer product of claim 1, wherein the polymeric shell comprises a polymeric material selected from the group consisting of polyacrylates, polyethylenes, polyamides, polystyrenes, polyisoprenes, polycarbonates, polyesters, polyureas, polyurethanes, polyolefins, polysaccharides, epoxy resins, vinyl polymers, urea cross-linked with formaldehyde or gluteraldehyde, melamine cross-linked with formaldehyde, gelatin-polyphosphate coacervates optionally cross-linked with gluteraldehyde, gelatin-gum arabic coacervates, cross-linked silicone fluids, polyamines reacted with polyisocyanates, acrylate monomers polymerised via free radical polymerization, silk, wool, gelatine, cellulose, alginate, proteins, and combinations thereof.

4. The consumer product of claim 1, wherein the polymeric shell comprises a polyacrylate.

5. The consumer product of claim 1, wherein the polymeric shell comprises a surface-modifying agent.

6. The consumer product of claim 5, wherein the surface-modifying agent is selected from cetyl trimethylammonium bromide (CTAB), polyvinyl alcohol) (PVA), polyvinyl pyrrolidone) (PVP), and mixtures thereof.

7. The consumer product of claim 1, wherein at least some of said particles are adsorbed on said surface-modifying agent.

8. The consumer product of claim 1, wherein the polymeric shell is obtained by an emulsification process in which a surface-modifying agent is employed as an emulsifier.

9. The consumer product of claim 1, wherein the first metal is palladium, platinum, silver, gold, copper, nickel, tin or a combination thereof; and the second metal is silver, gold, nickel, copper or a combination thereof.

10. The consumer product of claim 1, wherein the density of said particles on the polymeric shell is such that said particles cover from 0.1 to 80% of the surface area of the polymeric shell.

11. The consumer product of claim 1, wherein (i) the first metal is platinum and the second metal is gold; (ii) the first metal is gold and the second metal is silver; or (iii) the first metal is gold and the second metal is copper.

12. The consumer product of claim 1, wherein the metallic coating has a maximum thickness of 500 nm; and the metallic coating has a minimum thickness of 1 nm.

13. The consumer product of claim 1, wherein the coated microcapsule has a particle size of from 0.1 micron to 500 microns.

14. The consumer product of claim 1, wherein said composition is a personal care composition and, wherein said adjunct ingredient comprises a mixture of materials, said mixture comprising:
i) from 50% to 99.9%, by weight of the composition, of ethanol; and
ii) from 0.5% to 50% of a fragrance.

15. The consumer product of claim 1, wherein:
i) the polymeric shell comprises a polyacrylate;
ii) the polymeric shell comprises a surface-modifying agent, and wherein the surface-modifying agent is selected from cetyl trimethylammonium bromide (CTAB), polyvinyl alcohol) (PVA), polyvinyl pyrrolidone) (PVP), and mixtures thereof;
iii) the particles of the first metal are nanoparticles, wherein said nanoparticles have a particle size of less than 100 nm;
iv) the first metal is platinum and the second metal is gold, the first metal is gold and the second metal is silver, or the first metal is gold and the second metal is copper;
v) the coated microcapsule has a particle size of from 0.1 micron to 500 microns;
vi) the liquid core material comprises a perfume oil; and
vii) the adjunct ingredient comprises from 0.01% to 98%, by weight of the composition of ethanol.

16. A method of making a composition, said method comprising the steps:
combining an adjunct material with a plurality of coated microcapsules to form a composition;
wherein said coated microcapsules comprise
i) a microcapsule comprising a polymeric shell and a liquid core material encapsulated therein; and
ii) a metallic coating surrounding said microcapsule;
wherein the metallic coating comprises sterically stabilized nanoparticles of a first metal having a particle size of less than 100 nm adsorbed on said polymeric shell to form a discontinuous layer and a continuous film of a second metal overlaid onto the discontinuous layer by electroless plating catalyzed by the nanoparticles of the first metal;
wherein the sterically stabilized nanoparticles of a first metal are first neutral metal nanoparticles on the surfaces of which are adsorbed and coated a polymeric stabilizer;
wherein the metallic coating has a maximum thickness of 1000 nm;
wherein the continuous film of a second metal is substantially uniform; and
the coated microcapsules retain more than 50% by weight of the liquid core material as shown by an ethanol stability leakage test comprising combining the coated microcapsules in an aqueous solution of one part water and four parts ethanol to form a test mixture, exposing the text mixture to heat at 40° C. for seven days, thereafter separating the text mixture into the coated microcapsules and an aqueous test solution, and analyzing the aqueous test solution to determine the amount of liquid core material that has leached from the coated microcapsules wherein said composition is a component of a consumer product.

* * * * *